US006924413B2

United States Patent
Katsuyama

(10) Patent No.: US 6,924,413 B2
(45) Date of Patent: Aug. 2, 2005

(54) EXPERIMENTAL ANIMALS FOR EVALUATION OF THERAPEUTIC EFFECTS ON CORNEAL EPITHELIAL DAMAGES

(75) Inventor: Iwao Katsuyama, Osaka (JP)

(73) Assignee: Biochemical and Pharmacological Laboratories, Inc., Tondabayashi (JP)

(*) Notice: Subject to any disclaimer, the term of this patent is extended or adjusted under 35 U.S.C. 154(b) by 179 days.

(21) Appl. No.: 10/043,366

(22) Filed: Jan. 10, 2002

(65) Prior Publication Data

US 2003/0041339 A1 Feb. 27, 2003

(30) Foreign Application Priority Data

Mar. 30, 2001 (JP) ........................................ 2001-101250
Jul. 26, 2001 (JP) ........................................ 2001-226460
Nov. 28, 2001 (JP) ........................................ 2001-363147

(51) Int. Cl.$^7$ ............................................. A01K 67/00
(52) U.S. Cl. ............................................................. 800/9
(58) Field of Search ............................................. 800/9

(56) References Cited

U.S. PATENT DOCUMENTS 5,900,407 A * 5/1999 Yerxa et al. .................. 514/47

FOREIGN PATENT DOCUMENTS

JP  09-124505   5/1997   .......... A61K/38/44
JP  09-136832   5/1997   .......... A61K/31/19

OTHER PUBLICATIONS

BSS, www.home.intekom.com/pharm/alcon, Balanced Salt Solution.*
Gilbard et al., Morphologic effect of hyperosmolarity on rabbit corneal epithelium, 1984, OPTHALMOLOGY, vol. 91, pp. 1205–1212.*
Fujihara et al., establishment of a rabbit short–term dry eye model, 1995, Journal Of Ocular Pharmacology, vol. 11, pp. 503–508.*
Gans, The eye, 1970, Biology Of The Reptilia, vol. 2, pp. 1–97.*
Indu Arora et al., Ophthalmology, vol. 101, No. 12, Dec. 1994, pp. 1935–1940.
Daniel Meller et al., Opthalmic Research vol. 28, No. 2, 1996, pp. 71–79.
Jeffrey W. Ruberti et al., Investigative Opthalmology & Visual Science, Aug. 2000, vol. 41, No. 9, pp. 2523–2530.
Uno T. et al., IVOS, vol. 42, No. 4, pp. S263, 2001.
Peter M. Andrews et al., Cornea, vol. 13, No. 3, pp. 253–258, 1994.
Burgalassi et al.; Ophthalmic Research; vol. 31; No. 3; 1999 pp. 229–235; XP001030110.
Tsubota et al.; British Journal of Ophthalmology; vol. 83; No. 4; Apr. 1999; pp. 390 395; XP002275298.
Karaki; Folia Ophthalmologica Japonica 1980 Japan; vol. 31; No. 8; 1980; pp. 1324–1328; XP009028453.
Katsuyama et al.; Journal of Ocular Pharmacology and Therapeutics; vol. 19; No. 3; Jun. 2003; pp. 281–289; XP009028430.

* cited by examiner

Primary Examiner—Anne-Marie Falk
Assistant Examiner—Daniel M. Sullivan
(74) Attorney, Agent, or Firm—Birch, Stewart, Kolasch & Birch, LLP

(57) ABSTRACT

This invention provides experimental animals suffering corneal epithelial damages, such as dry eye, and methods of using the same to assay a variety of compounds for evaluating the therapeutic effect on the disease, and medicine selected using the method, wherein the corneal epithelial damage is induced by the steps of: using a water-absorbing material having a physical state selected from powder, solution, gel, jelly and tablet, and contacting the absorbing materials with the ocular cornea to generate a difference in osmotic pressure between the inside and outside of ocular corneal epithelium cells.

28 Claims, 12 Drawing Sheets

EXPERIMENTAL ANIMALS FOR EVALUATION OF THERAPEUTIC EFFECTS ON CORNEAL EPITHELIAL DAMAGES

REFERENCE TO RELATED APPLICATIONS

This application claims priority of Japanese Patent Application No. 2001-101250, filed Mar. 30, 2001, Japanese Patent Application No. 2001-226460, filed Jul. 26, 2001, and Japanese Patent Application No. 2001-363147, filed Nov. 28, 2001. The benefit under 35 USC §§ 119 (a–d) of the foregoing Japanese Patent Applications is hereby claimed, and the aforementioned applications are hereby incorporated herein by reference.

BACKGROUND OF THE INVENTION

1. Field of the Invention

The invention pertains to the field of experimental animals. More particularly, the invention pertains to experimental animals suffering corneal epithelial damages, such as dry eye, and methods of using the same to assay a variety of compounds for evaluating the therapeutic effect thereof on said disease.

2. Description of Related Art

The cornea is a transparent tissue of 0.52 to 1.0 mm thick, and constitutes together with the sclera an important barrier to foreign substances, and is organized into five layers: epithelium, Bowman's membrane, stroma, Descemet's membrane and endothelium.

The term "corneal epithelial damage" usually refers to a group of diseases in which the epithelium cells of the corneal epithelial layer, the forefront segments of the cornea, are partly or wholly impaired, damaged and/or abraded. Depending on the presence or absence of ulcers in the basement membrane or corneal stroma, the symptoms of these diseases are classified into superficial punctate keratopathy (SPK), simple corneal erosion, recurrent corneal erosion, and corneal abrasion. The diseases may be caused by lacrimal fluid disorders, diseases of eyelids and/or conjunctiva, metabolic disorders, infections, trauma, drugs, and the like. Among them, dry eye, which is caused by lacrimal fluid disorders, has been drawing much attention in recent years.

The term "dry eye" includes a group of diseases, which occur on the ocular surface, caused by the loss of lacrimal fluid.

Lacrimal fluid plays an important role in helping an ocular function normally. For example, 1) it keeps keratoconjunctiva moist or protects it from being dried; 2) the lacrimal fluid layer keeps the surface of the cornea smooth and functions as a transparent optical refractive medium; 3) antibacterial ingredients in lacrimal fluid prevent viral infection, bacterial infection and so on; 4) it flushes out foreign substances and/or wastes adhered to the surface of the keratoconjunctiva; 5) it supplies oxygen, water and nutrients to the cornea, one of the few tissues having no blood vessel therein; 6) it makes the blinking or ocular movement smooth; and 7) it functions as a migration path for leukocytes in cases of ocular trauma.

The surface of the eyeball in a healthy condition is worn by lacrimal fluid. A layer of new lacrimal fluid (lacrimal fluid layer) is formed at every blinking, so that the ocular surface is protected from drying. While this lacrimal fluid layer begins to dry in approximately ten seconds, the sensory nerve distributed over the ocular surface detects drying and induces blinking, thereby keeping the ocular surface always moistened with lacrimal fluid. This mechanism is known as a basal secretion of lacrimal fluid, and is distinguished from a reflex secretion, which occurs when sad or when dust gets into the eye. The surface of the keratoconjunctiva will get dry and be damaged if the volume of lacrimal fluid decreases.

Dry eye has been called an ocular xerosis or a hypolacrimia, which for the most part has been considered as one symptom of Sjogren's syndrome. However, types of dry eye, which impair only the basal secretion without Sjogren's syndrome, due to the use of VDT (visual display terminal, or simply "display"), are increasing in recent years.

In a visual information society of these days, the number of VDT workers is increasing rapidly in parallel with the growing use of OA apparatus including computers. The total number of dry eye patients in Japan now is estimated to be from one million to two million, and the number of patients is still increasing, including potential dry eye patients.

The frequency of blinking will decrease when people continue watching the display (VDT) of OA apparatus for a long hour. Since lacrimal fluid is supplied to the ocular surface while the eye is closed by blinking, said decrease in the frequency of blinking leads to reduction in volume of lacrimal fluid, and is causative of corneal damages. It is expected therefore that the number of dry eye patients will continue to increase due to the heavy burden to be imposed on eyes.

Besides the decrease in said blinking frequency brought about by the above VDT work, endogenous diseases, such as Sjogren's syndrome, dry keratoconjunctivitis and Stevens-Johnson syndrome, are causative of dry eye. Cataract operation, medicines, trauma, contact lenses and others may also be causative of dry eye, due to the quantitative or qualitative deterioration of lacrimal fluid.

Various medicines for treatment of the corneal epithelial damages, such as dry eye, have been made available on the market. However, the therapeutic effects of these medicines are unsatisfactory to meet with medical needs, and R & D of new medicines is extensively in progress. Such R & D of new medicines cannot be accomplished without suitable systems or model animals for evaluating the effect of each test compound on the corneal epithelial damages.

Known experimental model animals suffering corneal epithelial damage include a rat Vitamin A-deficient model (Japan Patent Publication No. H09-136832). In this model, a dry eye-like symptom is produced by breeding rats under Vitamin A-deficient conditions, and is healed by giving Vitamin A to said rats (oral or eye drop administration). Thus, these malnutritional model animals are still unsuitable to evaluate medicines having various mechanisms of action.

Other known model animals in this field include those whose corneal epithelial damages are produced by treatment with iodine gas or an organic solvent (e.g., n-heptanol); by physical treatment with, for example, a knife; or by alkali corrosion treatment using, for example, sodium hydroxide. Like dry eye, these model animals suffer corneal epithelial damages; however, said damages produced by the above-mentioned methods are healed within a short period of time and are inconvenient to evaluate the therapeutic effects of medicines. Thus, the development of model animals having prolonged corneal epithelial damages, which resist various medical treatment, have long been desired. (See Teruo Nishida "Development of Medicine; vol. 9; Search for Medicine I", pp. 287–291, published by Hirokawa Shoten, Tokyo, Japan (1990)).

Further known model animals in this field include a rabbit model which is produced by the compulsive eyelid retraction method (rabbit compulsive eyelid retraction model) (Kei Nagano et al., New Ophthalmology, 13 (2), pp. 267–270(1996)). In this model, the upper and lower eyelids of both eyes are everted under general anesthesia, are sutured, and are retracted compulsively for three hours. Said air-drying step deprives lacrimal fluid of water on the ocular surface, resulting in decrease in the water content of the ocular tissues, and the model animals thus obtained show dry eye-like symptoms. As seen from the above, this model animal is prepared by mechanisms similar to "dry eye" itself and, as compared with other model animals mentioned above (e.g., rat Vitamin A-deficient model), is more appropriate to be used for the assay of medicines having various mechanisms of action.

This model animal, however, is still unsatisfactory in that 1) it takes a long time, about 3 hours, to produce the model; 2) it is hard to steadily produce model animals having a predetermined damage on the surface of the cornea; 3) the corneal damage is not uniform on its surface; and 4) said damage is not maintained for a period of time sufficient to evaluate the therapeutic effect of medicines, as it is healed easily when moistened with lacrimal fluid by blinking.

SUMMARY OF THE INVENTION

Under the circumstances mentioned above, an object of the present invention is to provide an experimental animal, which is useful to evaluate the therapeutic effect of a medicine on corneal epithelial damages such as dry eye. Another object of the present invention is to provide said experimental animal, which makes it possible to control or adjust in advance the degree of said damages on the corneal surface. Other object or objects of the invention is/are to provide said experimental animal which can maintain the corneal epithelial damages for a period of time sufficient to evaluate the therapeutic effect of the medicine and thereby makes it possible to express said therapeutic effect quantitatively, for example, in terms of ED50 and the like. Further object of the present invention is to provide a method of screening or evaluating a medicine for the treatment or improvement of the corneal epithelial damages such as dry eye.

Still further objects, features and advantages of the present invention will become apparent from the following detailed description and the claims. It should be understood, however, that the detailed description and examples given below, while indicating preferred embodiments, should not be considered limited in any way as various changes and modifications within the spirit and scope of the invention will become apparent from this detailed description to persons skilled in the art.

MEANS TO SOLVE THE PROBLEM

The invention related to Claim 1 is an experimental animal having the corneal epithelial damage, wherein said corneal epithelial damage is caused by contacting the ocular cornea of said animal with a water-absorbing material and thereby generating the difference in osmotic pressure between the inside and outside of the ocular corneal epithelium cells.

The invention related to Claim 2 is the experimental animal claimed in Claim 1, wherein said corneal epithelial damage is dry eye.

The invention related to Claim 3 is the experimental animal claimed in Claim 1, wherein the water-absorbing material is contacted either with the whole area of the ocular cornea or a part thereof, or with a pupil area of the ocular cornea.

The invention related to Claim 4 is the experimental animal claimed in Claim 3, wherein said corneal epithelial damage is dry eye.

The invention related to Claim 5 is the experimental animal claimed in Claim 3, wherein the experimental animal is a non-human mammalian or a fowl.

The invention related to Claim 6 is the experimental animal claimed in Claim 3, wherein the experimental animal is rabbit.

The invention related to Claim 7 is the experimental animal claimed in Claim 3, wherein said water-absorbing material is at least one of materials selected from the group consisting of a polyol, a salt, an amino acid, a peptide and a water-soluble polymer.

The invention related to Claim 8 is the experimental animal claimed in Claim 3, wherein said water-absorbing material is at least one of the materials selected from the soup consisting of a saccharide, an alkali metal salt and an alkali earth metal salt.

The invention related to Claim 9 is the experimental animal claimed in Claim 3, wherein said water-absorbing material is at least one of the saccharides selected from the group consisting of glucose, maltose, sucrose, fructose, dextran and starch.

The invention related to Claim 10 is the experimental animal claimed in Claim 3, wherein said water-absorbing material is used in the physical state selected from powder, solution, gel, jelly or tablet.

The invention related to Claim 11 is the experimental animal claimed in Claim 3, wherein the ocular cornea is covered with a water-impermeable membrane or film having a hole or boles therein, the membrane or film is placed on the ocular cornea so that the hole or holes in the membrane or film comes on around the pupil area thereof, and said water-absorbing material is contacted with the ocular cornea through said hole or holes of the membrane or film.

The invention related to Claim 12 is the experimental animal claimed in Claim 11, wherein said corneal epithelial damage is dry eye.

The invention related to Claim 13 is the experimental animal claimed in Claim 11, wherein the experimental animal is a non-human mammalian or a fowl.

The invention related to Claim 14 is the experimental animal claimed in Claim 11, wherein the experimental animal is rabbit.

The invention related to Claim 15 is the experimental animal claimed in Claim 11, wherein said water-absorbing material is at least one of materials selected from the group consisting of a polyol, a salt an amino acid, a peptide and a water-soluble polymer.

The invention related to Claim 16 is the experimental animal claimed in Claim 11, wherein said water-absorbing material is at least one of the materials selected from the group consisting of a saccharide, an alkali metal salt and an alkali earth metal salt.

The invention related to Claim 17 is the experimental animal claimed in Claim 11, wherein said water-absorbing material is at least one of the saccharides selected from the group consisting of glucose, maltose, sucrose, fructose, dextran and starch.

The invention related to Claim 18 is the experimental animal claimed in Claim 11, wherein said water-absorbing material is used in the physical state selected from powder, solution, gel, jelly or tablet.

The invention related to Claim 19 is the experimental animal claimed in Claim 3, wherein the water-absorbing material is contacted with the ocular cornea through a water-permeable or semi-permeable membrane or film.

The invention related to Claim 20 is the experimental animal claimed in Claim 19, wherein said corneal epithelial damage is dry eye.

The invention related to Claim 21 is the experimental animal claimed in Claim 19, wherein the experimental animal is a non-human mammalian or a fowl.

The invention related to Claim 22 is the experimental animal claimed in Claim 19, wherein the experimental animal is rabbit.

The invention related to Claim 23 is the experimental animal claimed in Claim 19, wherein said water-absorbing material is at least one of materials selected from the group consisting of a polyol, a salt, an amino acid, a peptide and a water-soluble polymer.

The invention related to Claim 24 is the experimental animal claimed in Claim 19, wherein said water-absorbing material is at least one of the materials selected from the group consisting of a saccharide, an alkali metal salt and an alkali earth metal salt.

The invention related to Claim 25 is the experimental animal claimed in Claim 19, wherein said water-absorbing material is at least one of the saccharides selected from the group consisting of glucose, maltose, sucrose, fructose, dextran and starch.

The invention related to Claim 26 is the experimental animal claimed in Claim 19, wherein said water-absorbing material is used in the physical state selected from powder, solution, gel, jelly or tablet.

The invention related to Claim 27 is a method of screening or evaluating a medicine for treatment or improvement of a corneal epithelial damage, which comprises the steps of: contacting the ocular cornea of an experimental animal with a water-absorbing material and thereby generating a difference in osmotic pressure between the inside and outside of the ocular corneal epithelium cells to produce the corneal epithelial damage; administering a medicine to the damaged ocular cornea; and evaluating the therapeutic effect thereof on the corneal epithelial damage.

The invention related to Claim 28 is the method claimed in Claim 27, wherein said corneal epithelial damage is dry eye.

The invention related to Claim 29 is the experimental animal claimed in Claim 27, wherein the experimental animal is a non-human mammalian or a fowl.

The invention related to Claim 30 is the experimental animal claimed in Claim 27, wherein the experimental animal is rabbit.

The invention related to Claim 31 is the experimental animal claimed in Claim 27, wherein said water-absorbing material is at least one of materials selected from the group consisting of a polyol, a salt, an amino acid, a peptide and a water-soluble polymer.

The invention related to Claim 32 is the experimental animal claimed in Claim 27, wherein said water-absorbing material is at least one of the materials selected from the group consisting of a saccharide, an alkali metal salt and an alkali earth metal salt.

The invention related to Claim 33 is the experimental animal claimed in Claim 27, wherein said water-absorbing material is at least one of the saccharides selected from the group consisting of glucose, maltose, sucrose, fructose, dextran and starch.

The invention related to Claim 34 is the experimental animal claimed in Claim 27, wherein said water-absorbing material is used in the physical state selected from powder, solution, gel, jelly or tablet.

The invention related to Claim 35 is the method claimed in Claim 27, wherein the water-absorbing material is contacted either with the whole area of the ocular cornea or a part thereof, or with a pupil area of the ocular cornea.

The invention related to Claim 36 is the method claimed in Claim 35, wherein the ocular cornea is covered with a water-impermeable membrane or film having a hole or holes therein, the membrane or film is placed on the ocular cornea so that the hole or holes in the membrane or film comes on around the pupil area thereof, and said water-absorbing material is contacted with the ocular cornea through said hole or holes of the membrane or film.

The invention related to Claim 37 is the method claimed in Claim 35, wherein the water-absorbing material is contacted with the ocular cornea through a water-permeable or semi-permeable membrane or film.

The invention related to Claim 38 is the method claimed in Claim 27, wherein said method further includes the steps of: staining the damaged area of the ocular corneal epithelium either (a) after administration of the medicine, or (b) before and after administration of the medicine; and evaluating the therapeutic effect of said medicine, based on change in the stained area of the ocular corneal epithelium.

The invention related to Claim 39 is the method claimed in Claim 27, wherein the medicine is an eye drop.

The invention related to Claim 40 is the method claimed in Claim 38, wherein the medicine is an eye drop.

The invention related to Claim 41 is a medicine useful for treatment or improvement of a corneal epithelial damage, which is obtained, selected or evaluated by the method claimed in Claim 27.

The invention related to Claim 42 is a medicine useful for treatment or improvement of a corneal epithelial damage, which is obtained, selected or evaluated by the method claimed in Claim 38.

The invention related to Claim 43 is a method for making an experimental animal having corneal epithelial damage, comprising the step of contacting an ocular cornea of said animal with a water-absorbing material and thereby generating a difference in osmotic pressure between an inside and an outside of the ocular corneal epithelium cells.

BRIEF DESCRIPTION OF THE DRAWING

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

Figure 1:
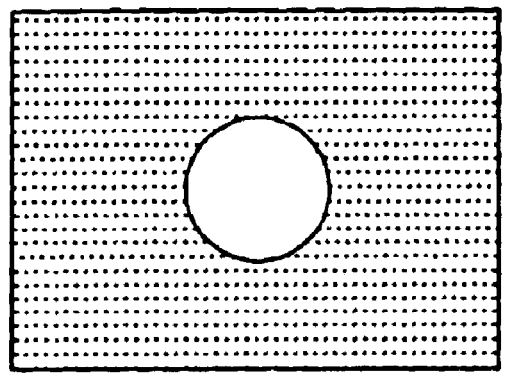
FIG. 1 is a schematic view of a square thin water-impermeable film used in producing the model animal example 1.

As described hereinbefore, the term "corneal epithelial damage" in this invention includes a group of diseases in which the corneal epithelial layer (the forefront segments of the cornea) or the corneal epithelium cells are partly or wholly impaired, damaged and/or abraded. Moreover, the term "dry eye" in this invention includes a group of symptoms which are caused by endogenous diseases such as ocular xerosis, Sjogren's syndrome and Stevens-Johnson syndrome, or exogenous causes such as surgical operation, medicines, trauma, contact lens, and the like. Dry eye is a typical example of such corneal epithelial damages.

The term "water-absorbing material" in this invention includes a variety of pharmacologically acceptable materials which can absorb water on the surface of cornea and generate the difference in osmotic pressure between the inside and outside of the ocular corneal epithelium cells. When such water-absorbing material contacts with the corneal surface, the osmotic pressure in the outside of the epithelium cells is higher than that in the inside of said cells. This leads to loss of the intracellular fluid from the corneal epithelium and produce the corneal epithelial damage.

In addition, the term "pharmacologically acceptable" in this invention means that the water-absorbing material exerts insignificant impact or influence on the living body of the animal or on the pharmacological properties of the medicine to be evaluated.

Any water-absorbing materials can be used to prepare the model animal of the present invention insofar as they have the above-mentioned properties. Such water-absorbing materials include, for example, polyols, salts, amino acids, peptides, water-soluble polymers, and the like. Preferred examples of said polyols include polyalcohols such as glycerin and ethylene glycol, monosaccharides such as glucose, galactose, mannose and fructose, oligo saccharides such as sucrose, lactose, maltose and cyclodextrin, polysaccharides such as starch, glycogen, dextran, pullulan and chitosan, and sugar alcohols such as glucitol, galactitol, mannitol and xylitol. Preferred examples of the salts include organic alkali metal salts such as sodium acetate, sodium citrate, potassium acetate and potassium citrate, inorganic alkali metal salts such as sodium chloride and sodium sulfate, organic alkali earth metal salts such as calcium acetate, magnesium acetate, calcium citrate, magnesium citrate, and inorganic alkali earth metal salts such as calcium chloride, magnesium chloride, potassium sulfate, magnesium sulfate, and the like. Preferred examples of the amino acids include glycine, alanine, valine, leucine, isoleucine, serine, threonine, aspartic acid, glutamic acid, asparagine, glutamine, lysine, hydroxyserine, arginine, cysteine, methionine, phenylalanine, tyrosine, tryptophan, histidine, proline, hydroxy proline and their derivatives. Preferred examples of the peptides include low molecular peptides such as glutathione, proteins such as albumin, globulin, collagen and gelatin, protein hydrolysates, and their derivatives. Further, preferred examples of water-soluble synthetic polymers include polyethylene glycol, polyethylene oxide, sodium polystyrenesulfonate, polyvinyl alcohol, polyvinylpyrrolidone and the like.

The above-mentioned water-absorbing material may be used either alone or in combination with two or more such water-absorbing materials. Furthermore, as described herein below, it may be used by blending with excipients, diluents, extenders, thickeners and so forth.

Any experimental animals may be used for the purpose of the present invention insofar as the eyeball of the animal has a size suitable for use in a pharmacological assay system. The animals to be used in this invention include, for example, non-human mammalians such as monkey, dog, cat, rabbit, guinea pig, rat, mouse, cow, sheep, pig, goat and the like, or fowls such as chicken, domestic duck, quail and so forth. Among them, mammalians such as monkey, dog, cat, rabbit, guinea pig, rat, mouse, cow, sheep, pig and goat are preferred as the model animals, as they are constantly supplied for experimental purposes and their physical conditions and breeding are readily controlled. Especially, rabbit, cat, dog, pig and goat are more preferable for use in the invention, for the size of their eyeballs are suitable for the experiment. While the breeding conditions of the animals are not restrictive and may be chosen in usual ways, each animal should preferably be bred under the same conditions before the experiments in order to obtain reproducible model animals.

A variety of methods may be used to prepare the model animal of the present invention, insofar as the model animal thus obtained is tolerable or endurable to the subsequent experiments. One preferable method of making such model animal of the invention is, for example, shown below.

The animal is anesthetized, and their eyelids are kept open. The eyelids can be kept open in conventional manners, for example, by fixing the upper and lower eyelids with an adhesive or an eyelid retractor. Then, the water-absorbing material is contacted with the ocular surface of the animal for an appropriate period of time. The experimental animal having the corneal epithelial damage is obtained by washing the ocular surface of said animal to remove the water-absorbing material therefrom.

The water-absorbing material may be contacted directly or indirectly with the surface of cornea in any known manners, and may also cover the whole surface of cornea or only a portion of said surface. The position on the corneal surface where the water-absorbing material is placed, as well as the size or shape of the area of the corneal surface where the water-absorbing material contacts, may vary depending on the kind of animal to be chosen or may be chosen as desired depending on the purposes of each experiments. For example, in contacting the water-absorbing material only with a portion of the corneal surface, the contact area may be in any geometric shape such as circle, ellipse, square, rectangle, triangle, star and other polygons, and the contact position may also be chosen as desired. To evaluate the therapeutic effect of a medicine quantitatively, however, it is preferable to place the water-absorbing material on or around the pupil area so that the contact area becomes a round shape.

The water-absorbing material may be used in the physical state of powder, solution, gel, jelly or tablet, and a suitable physical state of said material may be chosen depending on the physical properties of said material to be used and/or the purposes of each experiments.

In order to compare the therapeutic effect of each medicine quantitatively, experimental results should preferably be expressed in terms of numerical values such as ED50. According to this invention, such a result can be attained easily by controlling or adjusting the shape and size of the contact area, i.e., the area where the water-absorbing material contacts with the corneal surface. Such control or adjustment may be done, for example, by (1) covering the cornea with a water-impermeable membrane or film having a hole or holes in it, and placing the water-absorbing material on the water-impermeable membrane or film; or (2) mounting a cylindrical tube on the cornea, and placing the water-absorbing material into the tube. Any pharmacologically acceptable, water-impermeable membrane or film and tube may be use for this purpose. Examples of such membrane or film include those made of nylon, polyethylene, polypropylene, polystyrene, polycarbonate, polyvinyl chloride and polyfluoroethylene and the like, and examples of such tube include those made of metals such as aluminum, titanium and stainless steel, tree, bamboo and the like. To minimize background loss of fluid, it is usually preferable to avoid using materials which allow the intracellular fluid of eyeball, to permeate.

Contact of the water-absorbing material with the corneal surface may usually be carried out by putting said material directly on the corneal surface; but, if required, said material may be contacted indirectly with the corneal surface, e.g., through a water-permeable or semi-permeable membrane or film. The use of said water-permeable or semi-permeable membrane or film is advantageous in that, after contacted with the corneal surface, the water-absorbing material can be easily removed therefrom by simply peeling off the water-permeable or semi-permeable membrane or film from the corneal surface. Any pharmaceutically acceptable, water-permeable or semi-permeable membrane or film may be used for this purpose. Examples of such membrane or film include carbohydrate polymers such as cellulose or its derivatives, synthetic polymers such as polyvinyl alcohol, and the like. Said membrane or film may be used in any shapes, and preferably in the form of thin film so that it gives no substantial influence on the physical properties or functions of the water-absorbing material.

According to the present invention, the corneal epithelial damage can be produced all over the ocular surface. Alternatively, said damage with a pre-selected size can be made at a pre-selected area on the ocular surface by contacting the water-absorbing material with only a limited area of said surface. The latter method enables us to evaluate conveniently and precisely the therapeutic effect of the medicine, for in the latter case the change in therapeutic effects with time can be measured quantitatively as the change in the area of epithelial damage. For example, one preferred embodiment of the present invention comprises the steps of preparing a water-impermeable membrane or film having a hole or holes at around the center thereof, covering the ocular surface with said water-impermeable membrane or film so that the hole or holes in it comes on around the pupil area, and contacting the water-absorbing material with the ocular surface through said hole or holes of the membrane or film.

As described above, the water-absorbing material dehydrates ocular surface, and at the same time induces leakage of water from the ocular epithelium cells due to the difference in osmotic pressure between the inside and outside of the cells. To obtain suitable experimental animals of the invention, the difference in osmotic pressure between the inside and outside of the ocular corneal epithelium cells should preferably be kept at the level of not less than 0.5, more preferably at the level of not less than 1.0, further more preferably at the level of not less than 2.0, and most preferably at the level of not less than 3.0. When the water-absorbing material in the physical state of, e.g., powder, contacts with the corneal surface, it absorbs water on said surface and is dissolved in the fluid. The solution of said material obtained on the corneal surface is close to saturation and therefore generates the difference in osmotic pressure between the inside and outside of the corneal epithelium cells. Said difference in osmotic pressure induces leakage of the intracellular fluid through the semi-permeable cell membrane so as to dilute the hypertonic solution, and the fluid thus leaked out of the cell further serves to dissolve the remaining water-absorbing material. However, since the amount of the water-absorbing material to be used in the experiment usually exceeds over the volume of the intracellular fluid, this dissolution and leakage continues for a sufficient period of time and causes the corneal epithelial damages.

The difference in osmotic pressure between the inside and outside of the corneal epithelial cells varies depending on the water-absorbing material to be used. For example, a saturated fructose solution and a saturated sodium chloride solution have the osmotic pressure of about 2 and 20, respectively (a physiological saline solution and the intracellular fluid of corneal epithelium have the osmotic pressure of about 1) and hence, when contacted with the corneal epithelium cell, give rise to said "difference in osmotic pressure" of about 1 and 19, respectively.

In the present invention, the water-absorbing material may be used in admixture with excipients, diluents, extenders, and thickeners and so forth in order to adjust its osmotic pressure. Such excipients, diluents, extenders and thickeners may also be used to adjust the physical properties of the material or provide an appropriate size, shape, texture, etc. to the material. Crystalline cellulose, carboxymethylcellulose, carboxymethylethylcellulose, hydroxypropylcellulose, hydroxypropylmethylcellulose, wheat flour, wheat starch, wheat germ powder, rice powder, rice starch, potato starch, corn starch, corn starch granulation, carboxymethyl starch, hydroxypropyl starch, dextran, dextrin, agar, pectin, macrogol, gelatin and the like can be widely used for such purpose.

Suitable amount of the water-absorbing material to be contacted with the corneal surface may be readily chosen depending on the general knowledge and skills of persons having ordinary skill in this technical field.

The degree of corneal epithelial damage (i.e., the severity of symptoms) to be used for evaluation of the therapeutic effect should preferably be adjusted in advance, depending on the purposes of experiments. In the experimental animal of the invention, this adjustment can readily be done by making a suitable choice of the water-absorbing material, by changing the amount of the material, by formulating it with other ingredient(s) such as excipient(s) and the like, or by changing the contact time or the size of area of contact.

The water-absorbing material should be contacted with the corneal surface for a sufficient period of time to induce corneal epithelial damage. Such contact time usually should be 5 to 60 minutes, preferably 10 to 40 minutes, and more preferably 15 to 25 minutes. When such contact time is shorter than 5 minutes, insufficient damages may be induced on the corneal surface. On the other hand, it may make no sense to maintain contact for a period of time longer than 60 minutes, as the maximum epithelial damages are usually obtained in or within 60 minutes. In many cases, the contact time of 15 to 25 minutes is most preferable to obtain uniform pathologic conditions suitable for evaluation of medicines.

Thereafter, the water-absorbing material is removed from the ocular surface. Removal of the material from the ocular surface may be carried out in a conventional manner, for example, by washing the eye with the suitable amount of a pharmacologically acceptable liquid such as a physiological saline solution or an isotonic phosphate buffer solution. When the membrane, film, cylindrical tube or other instruments are used in the aforementioned step or steps, they are also removed from the ocular surface.

Said removal of the water-absorbing material may also be carried out without the above-mentioned washing step when the water-permeable or semi-permeable membrane or film is used in the experiment.

In the model animal of the present invention, the corneal epithelium is made dry by dehydration and shows the symptom of corneal abrasion. Without medical treatment etc., this symptom can not be recovered or improved even if the ocular surface is moistened with lacrimal fluid and lasts for a long period of time, for example, more than 10 hours or, in some cases, dozens of hours. This enables persons engaged in this art to evaluate the therapeutic effect of medicines.

Such characteristics of the invention are of significant importance in that the corneal surface of the known compulsive eyelid retraction model (three hour retraction) is simply kept dried without abrasion, the dry eye-like symptom of said animal recovers in about an hour owing to secretion of lacrimal fluid, and thus said known dry eye model has some difficulty in the use for pharmacological evaluation of compounds.

The present invention is also characteristic in that the animal model can be prepared within about 60 minutes, preferably 20 minutes, after the eyelid retraction, while the known method requires 3 hours or longer to generate the compulsive eyelid retraction model.

The present invention is further characteristic in that it enables us to make the animal model having a pre-selected size of damages on the corneal surface and evaluate quantitatively the change in severity of symptoms with time by simply measuring the change in the area of epithelial damage, while the known compulsive eyelid retraction model is not so suitable for use in quantitative evaluation of said change due to non-uniform damages formed on the corneal surface.

The "medicine" of the present invention includes any compounds, materials or compositions which are prepared and/or used for screening and/or evaluating their effect on corneal epithelial damages. It includes, of course, within its scope various drugs, quasi drugs or supplemental foods such as dietary supplements or functional foods, and should be construed not to be restricted to those which have already been available in the market. Potential medicines, i.e., those which are prepared and/or used only for research and/or development purposes, are also included within the scope of said "medicine" of the invention. Any such medicines include, for example, those which serve to protect from corneal epithelial damages, promote the recovery of corneal injuries, alleviate mucous membrane stimulus or protect mucous membrane. More specifically, it includes hyaluronic acid, chondroitin sulfate, dextran sulfate, adrenal cortical hormone and any other new medicines having new or known mechanism of action.

The medicine to be evaluated is usually administered in the form of eye drop to the eyeball. But, it may also be administered either orally or parenterally and, if administered parenterally, may be in the form of solution, suspension, ointment, injection, suppository and the like. Suitable dose of the medicine may be decided ad libitum based on an animal to be used and/or an age or body weight thereof. Conditions for administration such as timing and number of times thereof may also be decided depending on the medicine to be used and the purposes of experiments. For example, when used in the form of eye drop, the medicine is preferably administered for a few times every 30 minutes immediately after the model animal is prepared, and for a few times every one hour thereafter. Generally, it is preferred that the medicine is administered not less than 2 times, more preferably not less than 4 to 6 times, repeatedly.

Evaluation of the therapeutic effect of the medicine can be carried out in a conventional manner, for example, by observing reflection of light on the ocular surface, or by observing cells or tissues on the ocular surface with a microscope. To quantitatively evaluate such therapeutic effect, e.g., in terms of numerical values, it is preferred that the size or sizes in the area of ocular corneal epithelial damages is measured by staining the ocular cornea after administration of the medicine, and, if desired, said size of the damaged area is compared with the size in area of epithelial damages obtained in a control group (i.e., the group to which no medicine is administered) or with the size in the area of said damages measured before administration of the medicine (the stained area comparison method). Usually, as the damaged area or areas are stained selectively with dyes, the therapeutic effect of the medicine can be evaluated quantitatively in terms of the changes, e.g., percent decrease, in said stained area or areas. Any pharmacologically acceptable fluorochromes may be used for this purpose. Preferred examples of such fluorochrome include a fluorescein salt, rose bengal, sulfarodamine B, lissamine green and the like.

A method suitable to measure the stained area or areas may be readily chosen depending on the fluorochrome used in the experiment. For example, when a fluorescein salt is employed therein, the size of the stained area can be measured quantitatively according to conventional methods of measuring fluorescence intensity, or by processing and analyzing the image data of the ocular surface taken by digital camera.

One of practical embodiments for use in evaluating the therapeutic effect of the medicine may be shown below just for illustrative purpose.

The ocular surface of the model animal of the invention is well washed with a physiological saline solution, and incubated with an aqueous sodium fluorescein solution (e.g., a 2% solution). The ocular surface is again well washed with the physiological saline solution to remove free dye. The picture of the ocular surface is taken by digital camera. The image data thus obtained are processed by the use of an image-analyzing software, whereby the size of the stained area, i.e., the size in area of the corneal damages, is expressed in terms of the number of pixels. The therapeutic effect of the medicine can be calculated by comparing the sizes of the damaged area obtained before and after administration of the medicine.

Further, said therapeutic effect may also be evaluated by measuring the time required to heal the damages if the dose number is kept constant, or by counting the dose numbers to heal the damages if the medicine is administered at constant intervals.

EXAMPLES

The following examples are provided merely to illustrate the invention, and are not to be interpreted as limiting the scope of the invention which is described in the specification and claims.

Example 1

Production of the Model Animal Example 1

Rabbits (New Zealand white, male, 13 weeks old, about 3 kg body weight) were quarantined and habituated. They were bred in animal-breeding boxes set in a homothermal and homohumid room (room temperature of 21±3° C.; relative humidity of 50±20%, 12 hours illumination (7 a.m. light-up, 7 p.m. lights-out); and 10–15 times ventilation/hour). They were freely given the commercial feed (manufactured by Oriental Yeast Co., Ltd; RC4) and water (sterilized and filtered through the membrane having pore size of 0.2 µm in diameter). The animals were anaesthetized by intramuscular injection of 20 mg/kg of ketamine hydrochloride (manufactured by Sankyo Co., Ltd under the trade name "Ketaral 50 for intramuscular injection") and 10 mg/kg of xylazine hydrochloride (manufactured by Bayer under the trade name "Seraktal 2% for injection to dog and cat"). The eyelids of the animal were kept open and glued with the adhesive for surgery (manufactured by Sankyo Co., Ltd. under the trade name "Aron alpha A (Sankyo)").

Each one of the eyeballs was covered with a of polyfluoroethylene sheet film (20×30 mm, 0.14 mm thick; see FIG. 1) having a hole of 8 mm ø in size at around the center thereof.

91 parts by weight of powder sugar (manufactured by Sankyo Shokuhin Co., Ltd; a mixture of sucrose and corn starch (97:3; w/w)) and 9 parts by weight of distilled water were kneaded together to give a clayey composition. 0.5 g of the water-absorbing material thus obtained, i.e., the clayey composition mentioned above, was placed on the opening (i.e., the hole) of the film covering the eyeball, and kept contacted uniformly with the ocular surface for 20 minutes. Thereafter, the film and clayey composition were removed from the ocular surface. Said ocular surface was well washed with a physiological saline solution, whereby the model animal example 1 was obtained.

Example 2

Production of the Model Animal Example 2

A model animal was produced by using powder sugar (manufactured by Sankyo Shokuhin Co., Ltd.; a mixture of sucrose and corn starch (97:3; w/w) as the water-absorbing material.

A quarantined and habituated animal (rabbit) was anaesthetized in the same manner as in Example 1, and further anaesthetized locally by instillation of an eye drop containing a 0.4% oxybuprocaine hydrochloride (manufactured by Senju Pharmaceutical Co., Ltd. under the trade name "Anenocurl"). Then, eyelid retraction was done using a Vanguard eyelid retractor.

The eyeball was covered with a polyfluoroethylene sheet film (21 mm ø, 0.2 mm thick; see FIG. 2) having a hole of 8 mm ø in size at around the center thereof. 1 g of the powder sugar was placed on the opening (the hole) of the film covering the eyeball for 20 minutes. Thereafter, the film and sugar were removed from the ocular surface. Said ocular surface was thoroughly washed with a physiological saline solution, whereby the model animal example 2 was obtained.

Example 3

Production of the Model Animal Example 3

A model animal was produced in the same manner as in Example 2 by using the powder of sodium chloride as the water-absorbing material.

1 g of sodium chloride powder having a particle size of less than 150 µm in diameter (sieved by using a standard sieve (Sieve No. 100) of Japanese Industrial Standard) was placed on the opening (the hole) of the film covering the eyeball. The film and sodium chloride were removed from the ocular surface, and then the ocular surface was thoroughly washed with a physiological saline solution, whereby the model animal example 3 was obtained.

Comparative Example 1

Production of the Comparative Model Animal Example 1

A quarantined and habituated animal (rabbit) was anaesthetized in the same manner as in Example 1, and the eyes were kept open for 3 hours by way of eyelid retraction using a Vanguard eyelid retractor. The comparative model animal example 1 was thereby obtained.

Comparative Example 2

Production of the Comparative Model Animal Example 2

A model animal was prepared in the same manner as in Example 1, except that 1 g of a water-absorbing polymer was used instead of powder sugar.

Powdery acrylic acid polymer, obtained from sanitary napkin "Sofy Active Support" (manufactured by Unicharm Corporation), was placed on the opening (the hole) of the film. Thereafter, the film and polymer were removed from the ocular surface. Said ocular surface was well washed with a physiological saline solution, whereby the comparative model animal example 2 was obtained.

Example 4

Use of the Model Animal Example 1 for Evaluation of Medicine

This test was carried out to confirm that the model animal (the model animal example 1) and the screening method of the present invention are adequate as an assay system or a method to evaluate the therapeutic effect of medicines on corneal epithelial damages such as dry eye.

<Administration of a Medicine>

A pharmaceutical formulation containing 0.1% sodium hyaluronate (made available by Santen Pharmaceutical Co., Ltd. under the trade name "Hyalein 0.1"; hereinafter referred to as "Hyalein") was used as a medicine to be tested.

The tests were carried out with respect to the following four groups, using four eyeballs (right and left eyeballs of two animals) per group. One drop (about 50 micro liters) of Hyalein was instilled repeatedly to the eyeballs of animals in Groups 1 to 3, and a physiological saline solution was instilled, instead of Hyalein, to the eyeballs of animals in Group 4.

Group 1: Instillation of drop was carried out at 30 minutes intervals for 6 hours, at an hour intervals for additional 6 hours, at 2 hours intervals for additional 12 hours and thereafter at 4 hours intervals.

Group 2: Instillation of drop was carried out at 30 minutes intervals for 6 hours, at 2 hours intervals for additional 18 hours and thereafter at 4 hours intervals.

Group 3: Instillation of drop was carried out at 4 hours intervals from 6 hours after the model animal was prepared.

Group 4: Instillation of drop was carried out at 30 minutes intervals for 6 hours, at an hour intervals for additional 6 hours, at 2 hours intervals for the next 6 hours and thereafter at 4 hours intervals.

In this experiment, administration of the medicine was discontinued when the recovery of the corneal damages such as dry eye was confirmed based on the data obtained. In addition, the animal was considered to have recovered from the disease when no stained area of the cornea, i.e., no damaged area thereof was observed according to the experiments mentioned below.

<Measurement of Damaged Area>

The damaged area of the cornea was stained by instillation of 50 µl of an aqueous 2% sodium fluorescein solution onto the ocular surface. The ocular surface was washed with a physiological saline solution, and the photograph thereof was taken by a digital camera The data obtained were analyzed by an image-analyzing software (Mitani Corporation's "WIN ROOF"), and the size of the stained area, i.e., the damaged area of the cornea, was counted as the number of pixels. The photographs were taken immediately before administration of the medicine.

Figure 3:
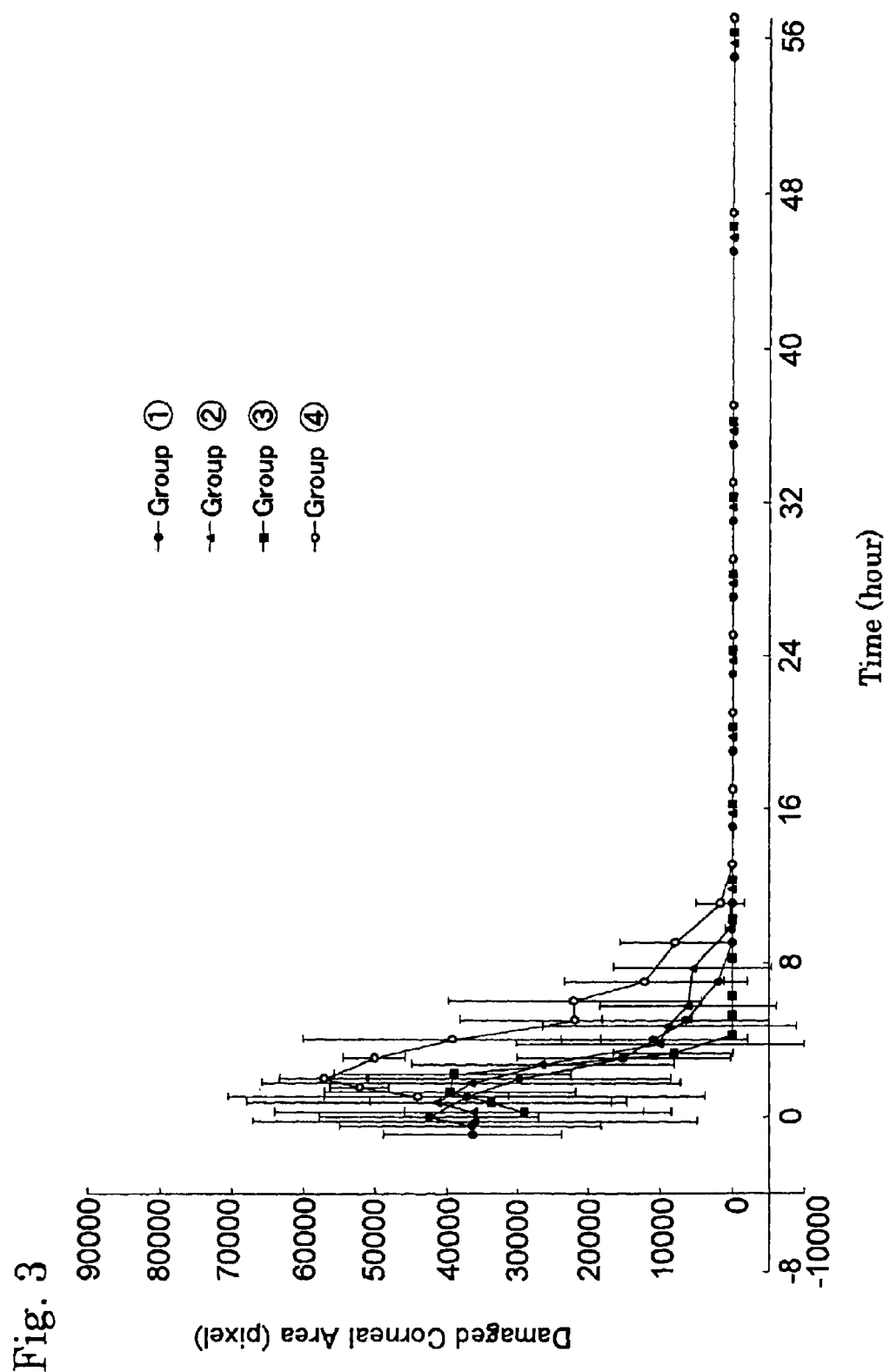
FIG. 3 is a graph showing a sequential change of the damaged corneal area measured according to Example 4.

The sequential changes in the damaged area of the cornea are shown in Table 1 and FIG. 3.

TABLE 1

Sequential Change of The Damaged Corneal Area

| Time (hour) | Group | Damaged Corneal Area (pixel) Average ± Standard deviation |
|---|---|---|
| 0 | ① | 36348.8 ± 12509.1 |
|   | ② | 35916.8 ± 31046.3 |
|   | ③ | 28074.5 ± 16729.8 |
|   | ④ | 44054.8 ± 12884.4 |
| 0.5 | ① | 36547.8 ± 18276.5 |
|   | ② | 36216.8 ± 27778.3 |
|   | ③ | 33650.5 ± 16918.2 |
|   | ④ | 52065.3 ± 4110.0 |
| 1 | ① | 42379.5 ± 15475.7 |
|   | ② | 41252.5 ± 26621.7 |
|   | ③ | 39483.0 ± 17584.4 |
|   | ④ | 57725.8 ± 6261.8 |
| 2 | ① | 37170.5 ± 33357.4 |
|   | ② | 36471.3 ± 29285.2 |
|   | ③ | 39002.8 ± 16725.0 |
|   | ④ | 49974.0 ± 4387.3 |
| 3 | ① | 29801.3 ± 21325.9 |
|   | ② | 26471.8 ± 18336.2 |
|   | ③ | 8134.5 ± 8223.8 |
|   | ④ | 39077.5 ± 20900.5 |
| 4 | ① | 15189.0 ± 14950.5 |
|   | ② | 10066.0 ± 20132.0 |
|   | ③ | 0.0 ± 0.0 |
|   | ④ | 21824.3 ± 18276.9 |
| 5 | ① | 10933.0 ± 12971.7 |
|   | ② | 8836.0 ± 17672.0 |
|   | ③ | 0.0 ± 0.0 |
|   | ④ | 22073.0 ± 17730.5 |
| 6 | ① | 6477.3 ± 11534.6 |
|   | ② | 6137.8 ± 12275.5 |
|   | ③ | 0.0 ± 0.0 |
|   | ④ | 12225.8 ± 11137.2 |
| 8 | ① | 1944.8 ± 3889.5 |
|   | ② | 5468.3 ± 10936.5 |
|   | ③ | 0.0 ± 0.0 |
|   | ④ | 7882.0 ± 7792.9 |
| 10 | ① | 0.0 ± 0.0 |
|   | ② | 308.5 ± 617.0 |
|   | ③ | 0.0 ± 0.0 |
|   | ④ | 1740.3 ± 3420.1 |
| 12 | ① | 0.0 ± 0.0 |
|   | ② | 0.0 ± 0.0 |
|   | ③ | 0.0 ± 0.0 |
|   | ④ | 34.0 ± 68.0 |
| 16 | ① | 0.0 ± 0.0 |
|   | ② | 0.0 ± 0.0 |
|   | ③ | 0.0 ± 0.0 |
|   | ④ | 0.0 ± 0.0 |
| 20 | ① | 0.0 ± 0.0 |
|   | ② | 0.0 ± 0.0 |
|   | ③ | 0.0 ± 0.0 |
|   | ④ | 0.0 ± 0.0 |
| 24 | ① | 0.0 ± 0.0 |
|   | ② | 0.0 ± 0.0 |
|   | ③ | 0.0 ± 0.0 |
|   | ④ | 0.0 ± 0.0 |
| 28 | ① | 0.0 ± 0.0 |
|   | ② | 0.0 ± 0.0 |
|   | ③ | 0.0 ± 0.0 |
|   | ④ | 0.0 ± 0.0 |
| 32 | ① | 0.0 ± 0.0 |
|   | ② | 0.0 ± 0.0 |
|   | ③ | 0.0 ± 0.0 |
|   | ④ | 0.0 ± 0.0 |
| 36 | ① | 0.0 ± 0.0 |
|   | ② | 0.0 ± 0.0 |
|   | ③ | 0.0 ± 0.0 |
|   | ④ | 0.0 ± 0.0 |
| 46 | ① | 0.0 ± 0.0 |
|   | ② | 0.0 ± 0.0 |
|   | ③ | 0.0 ± 0.0 |
|   | ④ | 0.0 ± 0.0 |
| 56 | ① | 0.0 ± 0.0 |

TABLE 1-continued

Sequential Change of The Damaged Corneal Area

| Time (hour) | Group | Damaged Corneal Area (pixel) Average ± Standard deviation |
|---|---|---|
| | ② | 0.0 ± 0.0 |
| | ③ | 0.0 ± 0.0 |
| | ④ | 0.0 ± 0.0 |

Figure 4:
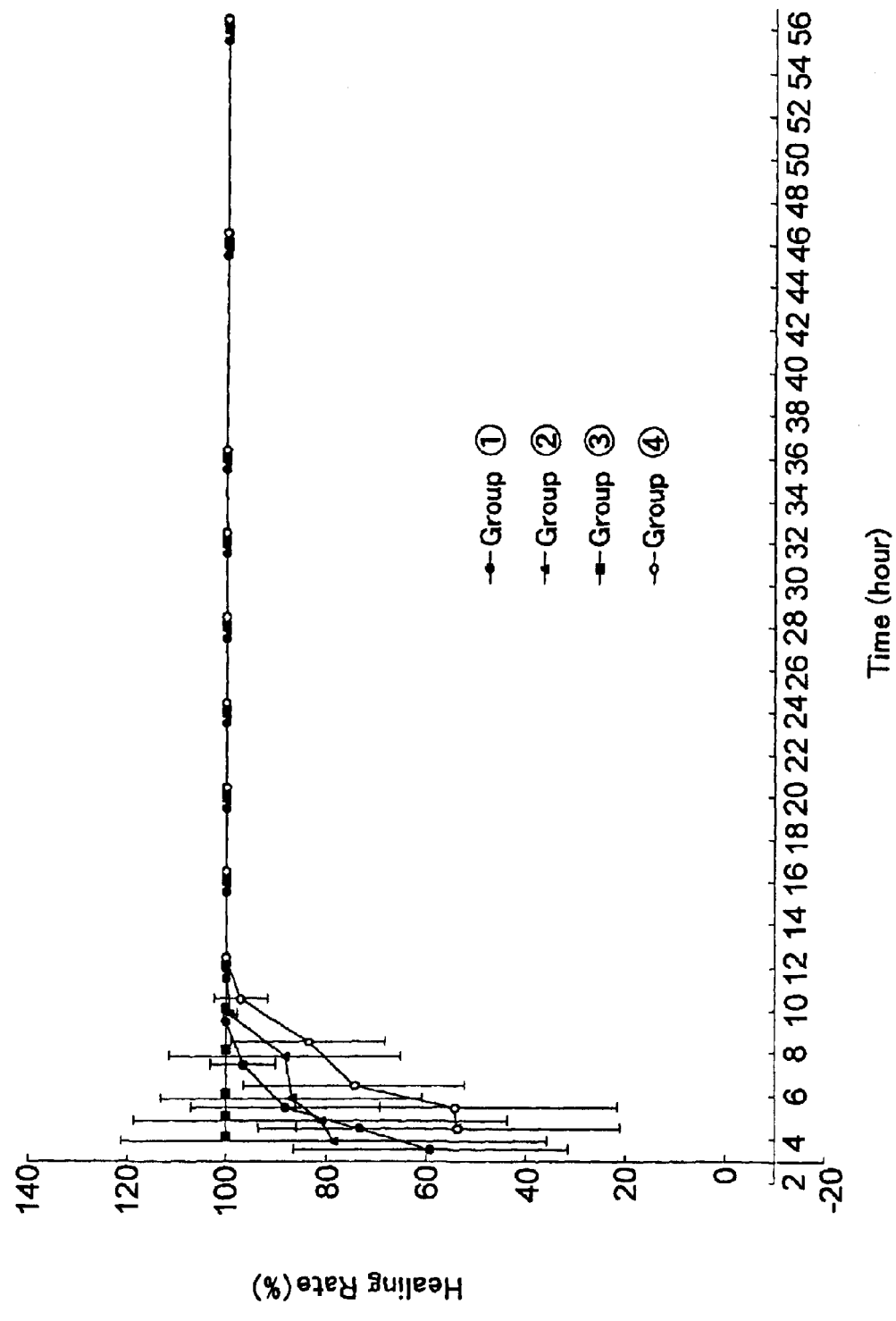
FIG. 4 is a graph showing a sequential change of the healing measured according to Example 4.

The sequential changes in the healing are shown in Table 2 and FIG. 4.

TABLE 2

Sequential Change of Healing Rate

| Time (hour) | Group | Healing Rate (%) Average ± Standard deviation |
|---|---|---|
| 4 | ① | 59.10 ± 27.50 |
| | ② | 78.58 ± 42.85 |
| | ③ | 100.00 ± 0.00 |
| | ④ | 53.60 ± 32.55 |
| 5 | ① | 73.33 ± 20.51 |
| | ② | 81.18 ± 37.65 |
| | ③ | 100.0 ± 0.00 |
| | ④ | 54.00 ± 32.39 |
| 6 | ① | 88.20 ± 18.93 |
| | ② | 86.93 ± 28.15 |
| | ③ | 100.00 ± 0.00 |
| | ④ | 74.35 ± 22.18 |
| 8 | ① | 96.75 ± 8.50 |
| | ② | 88.35 ± 23.30 |
| | ③ | 100.00 ± 0.00 |
| | ④ | 83.63 ± 15.32 |
| 10 | ① | 100.00 ± 0.00 |
| | ② | 99.35 ± 1.30 |
| | ③ | 100.00 ± 0.00 |
| | ④ | 97.25 ± 5.30 |
| 12 | ① | 100.00 ± 0.00 |
| | ② | 100.00 ± 0.00 |
| | ③ | 100.00 ± 0.00 |
| | ④ | 99.95 ± 0.10 |
| 16 | ① | 100.00 ± 0.00 |
| | ② | 100.00 ± 0.00 |
| | ③ | 100.00 ± 0.00 |
| | ④ | 100.00 ± 0.00 |
| 20 | ① | 100.00 ± 0.00 |
| | ② | 100.00 ± 0.00 |
| | ③ | 100.00 ± 0.00 |
| | ④ | 100.00 ± 0.00 |
| 24 | ① | 100.00 ± 0.00 |
| | ② | 100.00 ± 0.00 |
| | ③ | 100.00 ± 0.00 |
| | ④ | 100.00 ± 0.00 |
| 28 | ① | 100.00 ± 0.00 |
| | ② | 100.00 ± 0.00 |
| | ③ | 100.00 ± 0.00 |
| | ④ | 100.00 ± 0.00 |
| 32 | ① | 100.00 ± 0.00 |
| | ② | 100.00 ± 0.00 |
| | ③ | 100.00 ± 0.00 |
| | ④ | 100.00 ± 0.00 |
| 36 | ① | 100.00 ± 0.00 |
| | ② | 100.00 ± 0.00 |
| | ③ | 100.00 ± 0.00 |
| | ④ | 100.00 ± 0.00 |
| 46 | ① | 100.00 ± 0.00 |
| | ② | 100.00 ± 0.00 |
| | ③ | 100.00 ± 0.00 |
| | ④ | 100.00 ± 0.00 |
| 56 | ① | 100.00 ± 0.00 |
| | ② | 100.00 ± 0.00 |
| | ③ | 100.00 ± 0.00 |
| | ④ | 100.00 ± 0.00 |

TABLE 2-continued

Sequential Change of Healing Rate

| Time (hour) | Group | Healing Rate (%) Average ± Standard deviation |
|---|---|---|
| | ③ | 100.00 ± 0.00 |
| | ④ | 100.00 ± 0.00 |

<Data Analysis>

Figure 2:
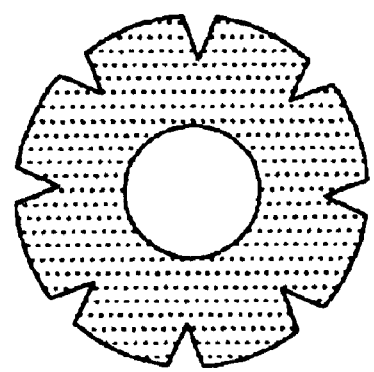
FIG. 2 is a schematic view of a circular thin water-impermeable film used in producing the model animal example 2.

As understood from the above Tables 1 & 2 and FIGS. 1 & 2, the model animals of the present invention were characterized by that the corneal damages thereof gradually worsened after the model animals were prepared, and the animals began to recover after the damages reached the maximum level. In this experiment, therefore, the evaluations of medicines were made using the maximum damage as a reference point.

Based on the results shown in Tables 1 and 2 and FIG. 3, the size in the area of damaged cornea which was measured 3 hours after the model animal was prepared was used as "Standard Area", and the area (the number of pixels) stained by sodium fluorescein was estimated as the damaged area of the cornea.

The "Healing Rate" in this invention was calculated according to the following formula:

$$\text{Healing Rate } (\%) = (SB - SP)/SB \times 100$$

SB: Standard Area (the number of pixels)

SP: Stained area (the number of pixels) measured each times during the above-mentioned experiments The results described above indicate that the model animal and screening method of the invention were adequate as an assay system or method to evaluate the therapeutic effects of medicines.

Example 5

Use of the Model Animal Example 2 for Evaluation of Medicine

This test was carried out to confirm that the model animal (the model animal example 2) and the screening method of the invention are adequate as an assay system or method to evaluate the therapeutic effect of medicines on corneal epithelial damages such as dry eye.

<Administration of a Medicine>

Hyalein was used as a medicine to be tested. The tests were carried out in the same manner as described in Example 4, using 4 groups of animals and four eyeballs (right and left eyeballs of two animals) per group. One drop (about 50 micro liters) of Hyalein was instilled repeatedly to the eyeballs of animals in Group 1 to 3, and a physiological saline solution to the eyeballs of animals in Group 4.

In the same manner as in Example 4, administration of the medicine was discontinued when the full recovery of the corneal damages was observed, and the animal was considered to have recovered from the disease when no damaged area of cornea was observed.

<Measurement of Damaged Area>

The damaged area was measured in the same manner as in Example 4. The sequential change in the damaged area of the cornea are shown in Table 3 and FIG. 5, and the sequential changes in the healing are shown in Table 4 and FIG. 6.

TABLE 3

Sequential Change of The Damaged Corneal Area

| Time (hour) | Group | Damaged Corneal Area (pixel) Average ± Standard deviation |
|---|---|---|
| 0 | ① | 24177.5 ± 4888.2 |
|  | ② | 14392.5 ± 12401.6 |
|  | ③ | 16154.5 ± 12128.7 |
|  | ④ | 18881.5 ± 15648.9 |
| 0.5 | ① | 27685.0 ± 7415.3 |
|  | ② | 19892.8 ± 14878.4 |
|  | ③ | 21058.0 ± 12773.5 |
|  | ④ | 28582.8 ± 12486.2 |
| 1 | ① | 28565.8 ± 7892.6 |
|  | ② | 27868.5 ± 21175.4 |
|  | ③ | 24483.8 ± 12824.4 |
|  | ④ | 36458.3 ± 10250.0 |
| 2 | ① | 28479.8 ± 13866.8 |
|  | ② | 28895.3 ± 20100.2 |
|  | ③ | 26142.5 ± 11445.9 |
|  | ④ | 40141.5 ± 5036.9 |
| 3 | ① | 32485.0 ± 11376.0 |
|  | ② | 31904.0 ± 18045.6 |
|  | ③ | 32550.0 ± 12879.9 |
|  | ④ | 42987.0 ± 3105.8 |
| 4 | ① | 36849.8 ± 20643.3 |
|  | ② | 36306.3 ± 20920.1 |
|  | ③ | 38326.3 ± 12968.0 |
|  | ④ | 45659.3 ± 3351.8 |
| 5 | ① | 31398.3 ± 16465.2 |
|  | ② | 27710.8 ± 12891.8 |
|  | ③ | 15474.0 ± 5260.3 |
|  | ④ | 38240.8 ± 14846.7 |
| 6 | ① | 26268.0 ± 12879.7 |
|  | ② | 22161.5 ± 17779.6 |
|  | ③ | 9398.5 ± 2381.3 |
|  | ④ | 32848.0 ± 13119.8 |
| 8 | ① | 23955.3 ± 12059.6 |
|  | ② | 20283.3 ± 16461.0 |
|  | ③ | 8827.8 ± 1744.1 |
|  | ④ | 31588.0 ± 13483.8 |
| 10 | ① | 23280.8 ± 12138.2 |
|  | ② | 18745.0 ± 16508.3 |
|  | ③ | 6427.3 ± 3005.5 |
|  | ④ | 29768.5 ± 12672.0 |
| 12 | ① | 21008.3 ± 9858.4 |
|  | ② | 16821.8 ± 15478.1 |
|  | ③ | 4176.3 ± 1997.4 |
|  | ④ | 26842.8 ± 11504.0 |
| 16 | ① | 17676.5 ± 9358.8 |
|  | ② | 13361.0 ± 13992.1 |
|  | ③ | 946.5 ± 1804.8 |
|  | ④ | 24393.8 ± 12068.2 |
| 20 | ① | 13657.8 ± 8482.4 |
|  | ② | 10269.5 ± 11804.1 |
|  | ③ | 153.3 ± 306.5 |
|  | ④ | 22043.8 ± 11541.8 |
| 24 | ① | 9928.5 ± 6287.7 |
|  | ② | 7064.3 ± 9245.2 |
|  | ③ | 0.0 ± 0.0 |
|  | ④ | 19452.5 ± 10993.0 |
| 28 | ① | 7281.8 ± 4708.0 |
|  | ② | 5260.8 ± 8363.1 |
|  | ③ | 0.0 ± 0.0 |
|  | ④ | 16235.8 ± 9710.3 |
| 32 | ① | 5359.3 ± 3855.6 |
|  | ② | 3601.0 ± 8849.3 |
|  | ③ | 0.0 ± 0.0 |
|  | ④ | 13900.8 ± 7458.9 |
| 36 | ① | 1187.5 ± 1361.9 |
|  | ② | 0.0 ± 0.0 |
|  | ③ | 0.0 ± 0.0 |
|  | ④ | 10643.5 ± 8630.7 |
| 46 | ① | 0.0 ± 0.0 |
|  | ② | 0.0 ± 0.0 |
|  | ③ | 0.0 ± 0.0 |
|  | ④ | 3871.0 ± 4747.4 |
| 56 | ① | 0.0 ± 0.0 |
|  | ② | 0.0 ± 0.0 |
|  | ③ | 0.0 ± 0.0 |
|  | ④ | 2228.8 ± 3179.9 |

TABLE 4

Sequential Change of Healing Rate

| Time (hour) | Group | Healing Rate (%) Average ± Standard deviation |
|---|---|---|
| 8 | ① | 5.03 ± 1.11 |
|  | ② | 9.15 ± 3.64 |
|  | ③ | 5.25 ± 4.80 |
|  | ④ | 5.18 ± 5.21 |
| 10 | ① | 8.90 ± 3.85 |
|  | ② | 19.10 ± 7.01 |
|  | ③ | 31.80 ± 27.63 |
|  | ④ | 10.93 ± 7.68 |
| 12 | ① | 16.48 ± 8.86 |
|  | ② | 27.88 ± 7.24 |
|  | ③ | 56.20 ± 18.09 |
|  | ④ | 19.58 ± 4.97 |
| 16 | ① | 32.35 ± 16.72 |
|  | ② | 47.70 ± 14.58 |
|  | ③ | 92.55 ± 13.85 |
|  | ④ | 29.43 ± 14.13 |
| 20 | ① | 49.80 ± 21.67 |
|  | ② | 63.38 ± 21.73 |
|  | ③ | 98.83 ± 2.35 |
|  | ④ | 36.70 ± 12.96 |
| 24 | ① | 64.08 ± 19.80 |
|  | ② | 77.10 ± 17.64 |
|  | ③ | 100.00 ± 0.00 |
|  | ④ | 45.18 ± 14.95 |
| 28 | ① | 73.75 ± 16.54 |
|  | ② | 84.90 ± 17.61 |
|  | ③ | 100.00 ± 0.00 |
|  | ④ | 54.73 ± 18.57 |
| 32 | ① | 80.80 ± 16.07 |
|  | ② | 91.50 ± 13.30 |
|  | ③ | 100.00 ± 0.00 |
|  | ④ | 60.80 ± 12.30 |
| 36 | ① | 96.35 ± 4.81 |
|  | ② | 100.00 ± 0.00 |
|  | ③ | 100.00 ± 0.00 |
|  | ④ | 73.03 ± 20.90 |
| 46 | ① | 100.00 ± 0.00 |
|  | ② | 100.00 ± 0.00 |
|  | ③ | 100.00 ± 0.00 |
|  | ④ | 90.48 ± 12.23 |
| 56 | ① | 100.00 ± 0.00 |
|  | ② | 100.00 ± 0.00 |
|  | ③ | 100.00 ± 0.00 |
|  | ④ | 94.38 ± 8.41 |

<Data Analysis>

Figure 5:
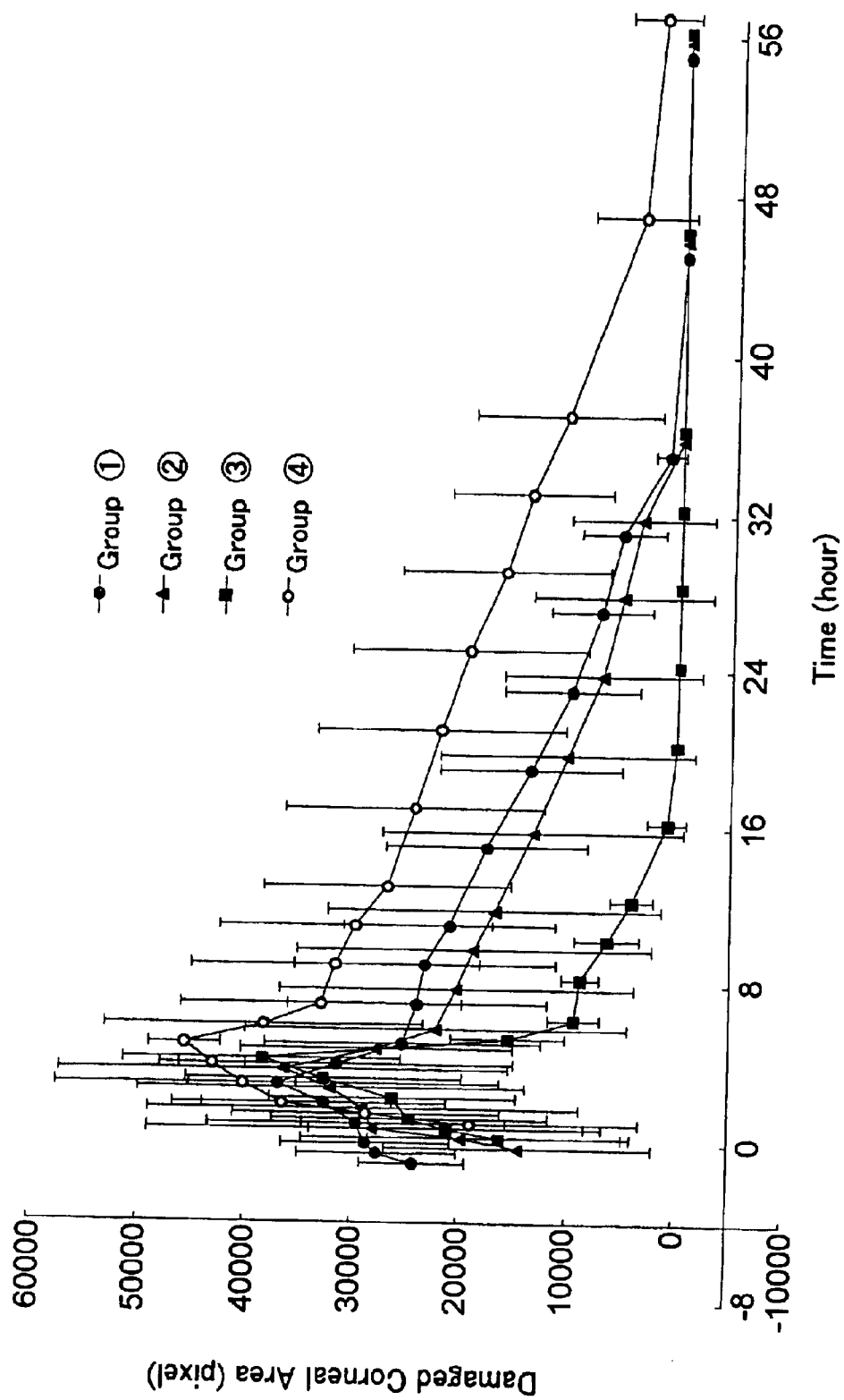
FIG. 5 is a graph showing a sequential change of the damaged corneal area measured according to Example 5.
Figure 6:
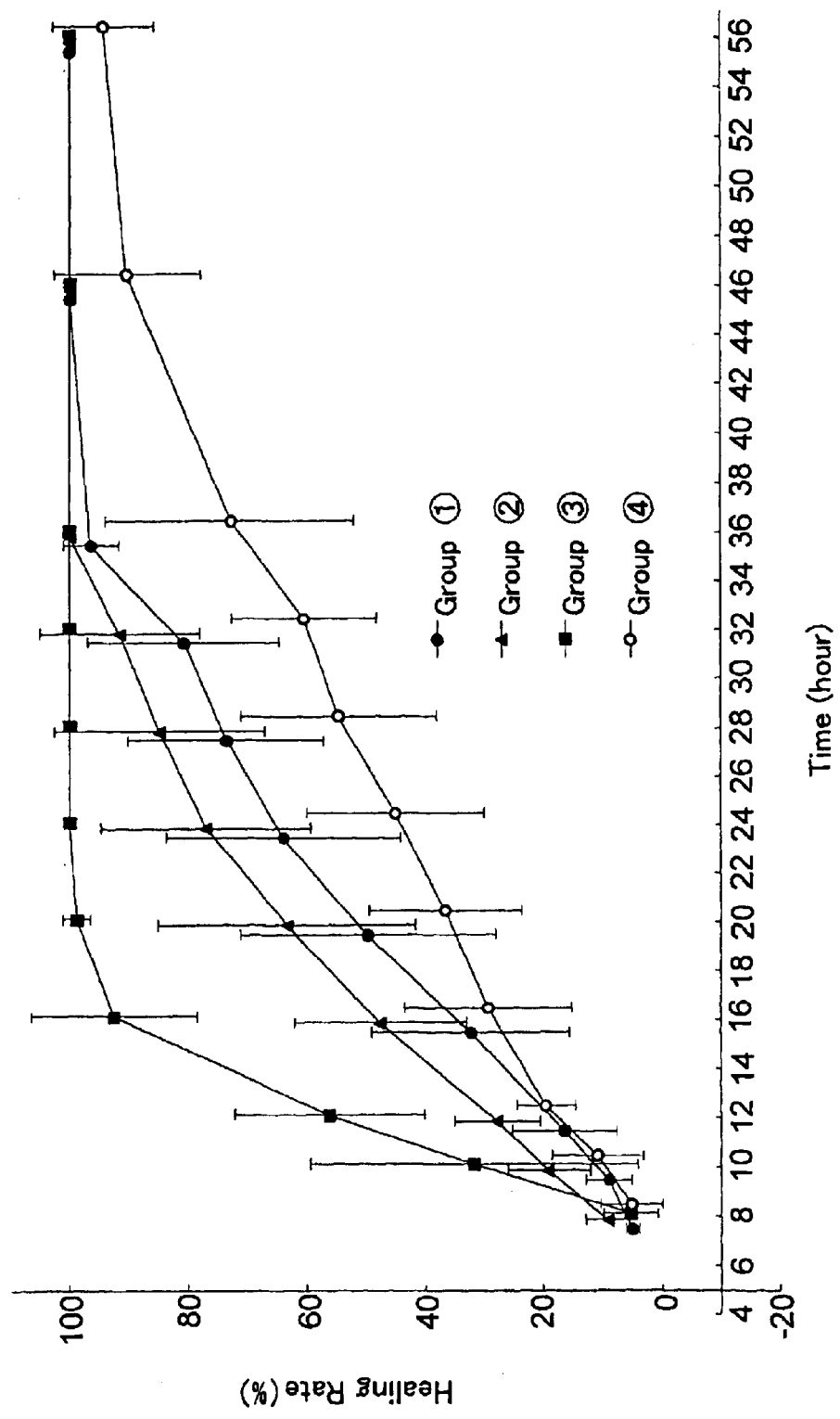
FIG. 6 is a graph showing a sequential change of the heating measured according to Example 5.

Based on the results shown in Table 3 and FIG. 5, the "Healing Rate" in the invention was calculated using as "Standard Area" the size in the area of damaged cornea which was measured 6 hours after the model animal was prepared. The formula shown in Example 4 was used for said calculation.

The results described above indicate that the model animal and screening method of the invention were adequate as an assay system or a method to evaluate the therapeutic effects of medicines.

Figure 7:
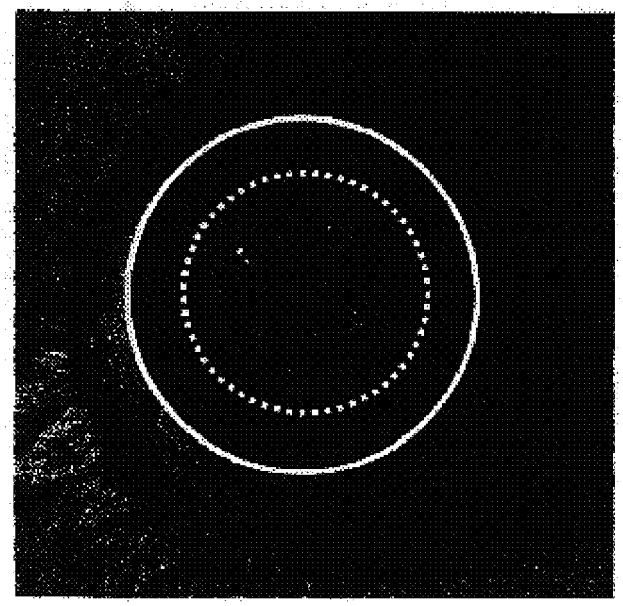
FIG. 7 is a photographic image of a typical ocular sample of the model animal example 2 (the photograph was taken immediately after the model animal was made).

The photographic image of a typical ocular sample, which was taken immediately after the model animal was prepared, is shown in FIG. 7. This indicates that uniform corneal epithelial damages, i.e., uniform area stained with sodium fluorescein, were formed in a round shape on the ocular surface of the model animal example 2.

Figure 8:
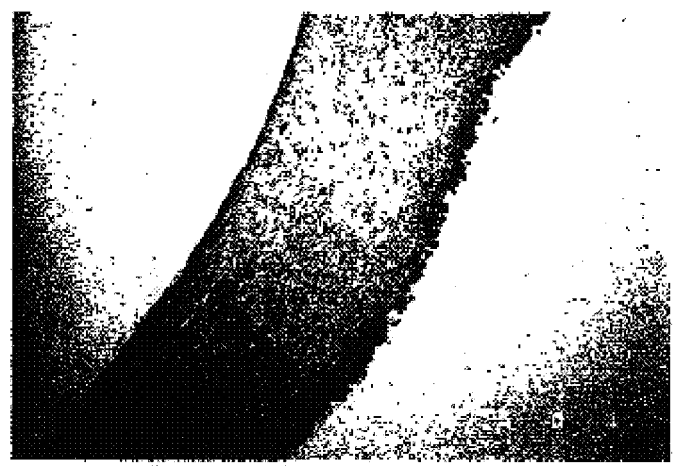
FIG. 8 is a H-E staining image (photographic magnifying power of 100) of a corneal section of the model animal example 2 (the photograph was taken immediately after the model animal was made).
Figure 9:
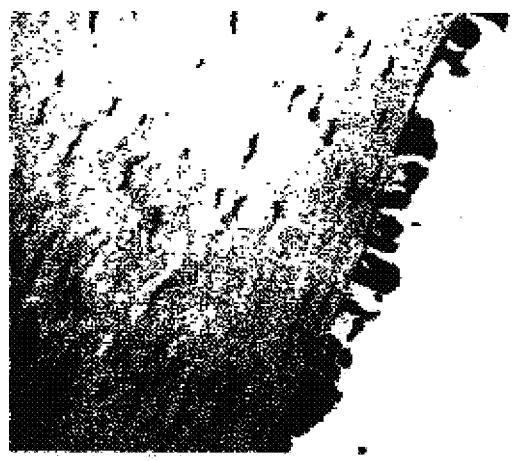
FIG. 9 is a H-E staining image (photographic magnifying power of 400) of a corneal section of the model animal example 2 (the photograph was taken immediately after the model animal was made).
Figure 10:
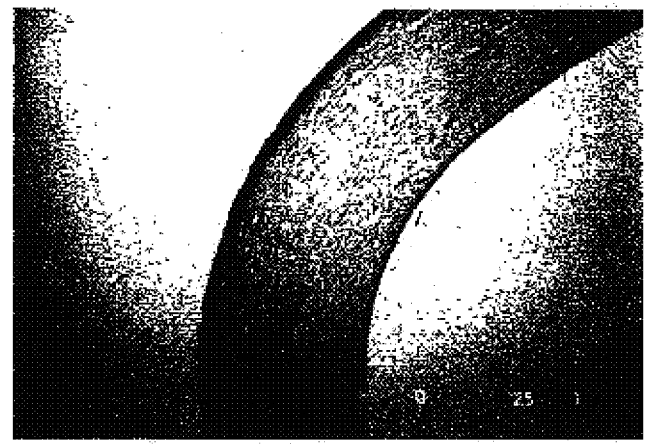
FIG. 10 is a H-E staining image (photographic magnifying power of 100) of a corneal section of the control animal (no corneal damage).
Figure 11:
FIG. 11 is a H-E staining image (photographic magnifying power of 400) of a corneal section of the control animal (no corneal damage).

The photographic images of corneal sections stained with hematoxylin-eosin (H-E), which were taken immediately after the model animal was prepared, are shown in FIG. 8 (photographic magnifying power of 100) and FIG. 9 (photographic magnifying power of 400). Just for comparison, the photographic images of corneal sections of a control animal (no medical treatment) stained with H-E are also shown in FIG. 10 (photographic magnifying power of 100) and FIG. 10 photographic magnifying power of 400). These images indicate that the uniform layer of epithelium cells were formed on the surface of cornea of said control animal, while the corneal epithelium cells in the model animal example 2 were widely injured, abraded and/or damaged.

Example 6

Use of the Model Animal Example 3 for Evaluation of Medicine

This test was carried out to confirm that the model animal (the model animal example 3) and the screening method of the invention are adequate as an assay system or method to evaluate the therapeutic effect of medicines on corneal epithelial damages such as dry eye.

<Administration of a Medicine>

Hyalein was used as a medicine to be tested. The tests were carried out in the same manner as described in Example 4 or 5, using 4 groups of animals and four eyeballs (right and left eyeballs of two animals) per group.

One drop (about 50 micro liters) of Hyalein was instilled repeatedly to the eyeballs of animals in Group 1 to 3, and a physiological saline solution to the eyeballs of animals in Group 4.

In the same manner as in Example 4 or 5, administration of the medicine was discontinued when the recovery of the corneal damages was observed, and the animal was considered to have recovered from the disease when no damaged area of cornea was observed.

<Measurement of damaged area>

The damaged area was measured in the same manner as in Example 1.

Figure 12:
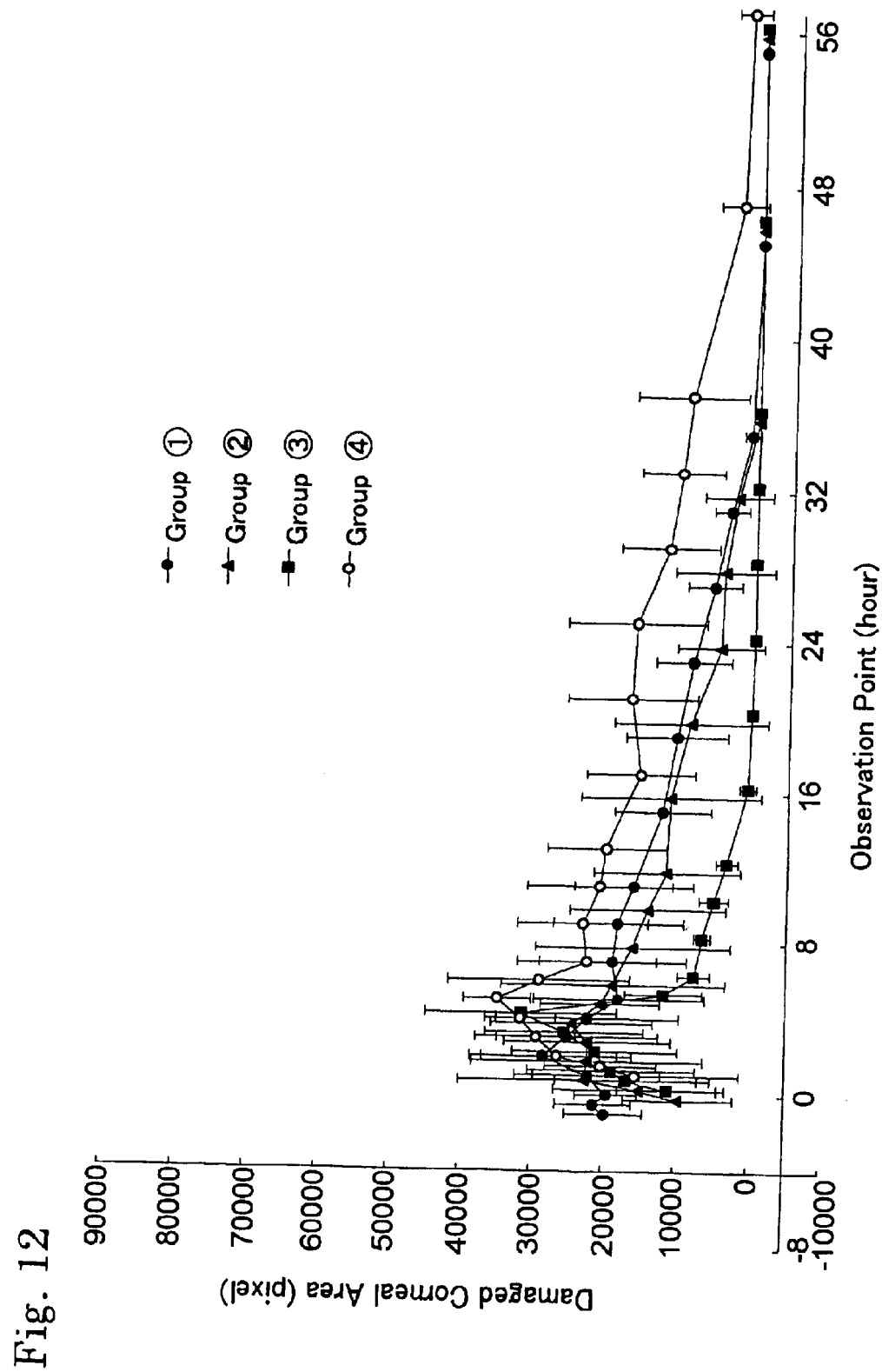
FIG. 12 is a graph showing a sequential change of the damaged corneal area measured according to Example 6.
Figure 13:
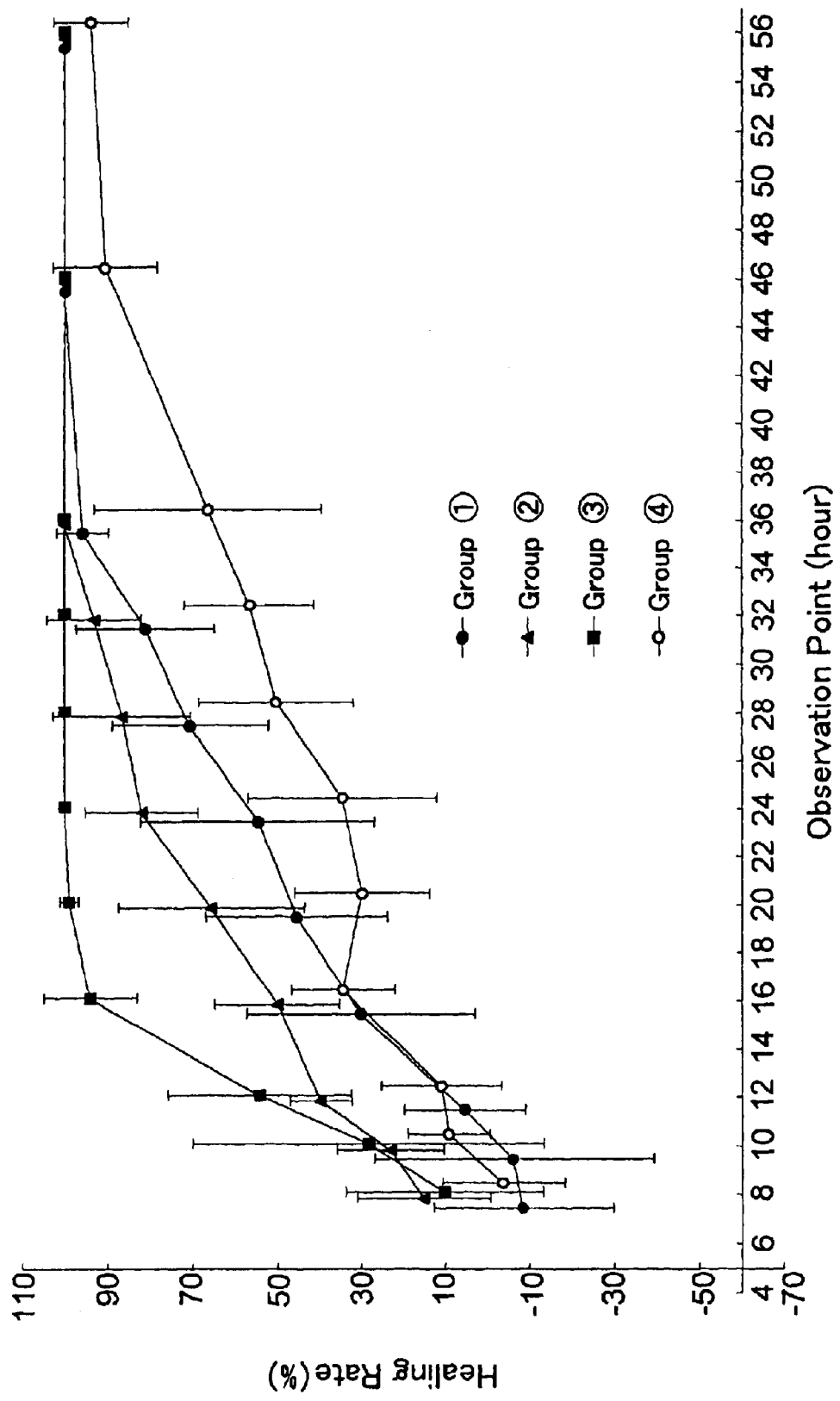
FIG. 13 is a graph showing a sequential change of the healing measured according to Example 6.

The sequential change in the damaged area of the cornea are shown in Table 5 and FIG. 12, and the sequential change in the healing are shown in Table 6 and FIG. 13.

TABLE 5

Sequential Change of The Damaged Corneal Area

| Time (hour) | Group | Damaged Corneal Area (pixel) Average ± Standard deviation |
|---|---|---|
| 0 | ① | 19728.5 ± 5410.6 |
|  | ② | 9495.0 ± 7484.4 |
|  | ③ | 11012.5 ± 6839.9 |
|  | ④ | 15464.5 ± 14249.5 |
| 0.5 | ① | 21246.3 ± 5283.4 |
|  | ② | 14930.8 ± 11849.3 |
|  | ③ | 15698.8 ± 9898.8 |
|  | ④ | 20215.5 ± 7808.0 |
| 1 | ① | 19397.8 ± 4290.0 |
|  | ② | 22550.0 ± 17454.9 |

TABLE 5-continued

Sequential Change of The Damaged Corneal Area

| Time (hour) | Group | Damaged Corneal Area (pixel) Average ± Standard deviation |
|---|---|---|
|  | ③ | 18772.5 ± 11663.0 |
|  | ④ | 26397.8 ± 10471.9 |
| 2 | ① | 22066.8 ± 10166.2 |
|  | ② | 22167.0 ± 16070.2 |
|  | ③ | 21103.8 ± 11529.1 |
|  | ④ | 28330.0 ± 5482.0 |
| 3 | ① | 28296.3 ± 10328.0 |
|  | ② | 22171.0 ± 11611.1 |
|  | ③ | 25376.3 ± 10997.5 |
|  | ④ | 31569.0 ± 4878.8 |
| 4 | ① | 25066.8 ± 12750.7 |
|  | ② | 24341.3 ± 11249.4 |
|  | ③ | 31479.8 ± 13328.2 |
|  | ④ | 34854.8 ± 4633.7 |
| 5 | ① | 22252.5 ± 12745.8 |
|  | ② | 20432.5 ± 8300.8 |
|  | ③ | 11709.5 ± 5351.2 |
|  | ④ | 29050.0 ± 12704.1 |
| 6 | ① | 17929.0 ± 11859.5 |
|  | ② | 18774.3 ± 15531.5 |
|  | ③ | 7571.0 ± 2157.3 |
|  | ④ | 22373.3 ± 9687.0 |
| 8 | ① | 18797.5 ± 10252.3 |
|  | ② | 16075.5 ± 13457.1 |
|  | ③ | 6528.8 ± 1118.1 |
|  | ④ | 22993.8 ± 9111.3 |
| 10 | ① | 18087.5 ± 8973.3 |
|  | ② | 14054.5 ± 10741.9 |
|  | ③ | 5010.0 ± 2026.3 |
|  | ④ | 20719.8 ± 10124.2 |
| 12 | ① | 16017.3 ± 8288.9 |
|  | ② | 11504.5 ± 10057.3 |
|  | ③ | 3351.3 ± 1526.8 |
|  | ④ | 19902.8 ± 8324.3 |
| 16 | ① | 12175.5 ± 6598.1 |
|  | ② | 11089.8 ± 12416.6 |
|  | ③ | 603.8 ± 1152.2 |
|  | ④ | 15293.5 ± 7506.5 |
| 20 | ① | 10373.8 ± 7026.2 |
|  | ② | 8550.5 ± 10594.5 |
|  | ③ | 113.0 ± 226.0 |
|  | ④ | 16648.0 ± 9017.7 |
| 24 | ① | 8291.5 ± 5193.3 |
|  | ② | 4625.3 ± 5887.1 |
|  | ③ | 0.0 ± 0.0 |
|  | ④ | 16107.0 ± 9616.5 |
| 28 | ① | 5556.5 ± 3665.2 |
|  | ② | 4179.3 ± 6852.1 |
|  | ③ | 0.0 ± 0.0 |
|  | ④ | 11759.8 ± 8736.9 |
| 32 | ① | 3451.0 ± 2358.5 |
|  | ② | 2542.0 ± 4702.1 |
|  | ③ | 0.0 ± 0.0 |
|  | ④ | 10245.3 ± 5647.8 |
| 36 | ① | 881.0 ± 1049.9 |
|  | ② | 0.0 ± 0.0 |
|  | ③ | 0.0 ± 0.0 |
|  | ④ | 9115.8 ± 7579.9 |
| 46 | ① | 0.0 ± 0.0 |
|  | ② | 0.0 ± 0.0 |
|  | ③ | 0.0 ± 0.0 |
|  | ④ | 2635.8 ± 3234.6 |
| 56 | ① | 0.0 ± 0.0 |
|  | ② | 0.0 ± 0.0 |
|  | ③ | 0.0 ± 0.0 |
|  | ④ | 1676.5 ± 2258.6 |

TABLE 6

Sequential Change of Healing Rate

| Time (hour) | Group | Healing Rate (%) Average ± Standard deviation |
|---|---|---|
| 8 | ① | -8.43 ± 21.35 |
| | ② | 15.15 ± 15.82 |
| | ③ | 10.13 ± 23.50 |
| | ④ | -3.83 ± 14.58 |
| 10 | ① | -6.15 ± 33.09 |
| | ② | 23.05 ± 12.71 |
| | ③ | 28.18 ± 41.73 |
| | ④ | 9.20 ± 9.73 |
| 12 | ① | 5.35 ± 14.35 |
| | ② | 39.60 ± 7.30 |
| | ③ | 54.13 ± 21.67 |
| | ④ | 10.93 ± 14.32 |
| 14 | ① | 30.15 ± 27.06 |
| | ② | 49.90 ± 14.77 |
| | ③ | 94.03 ± 10.91 |
| | ④ | 34.35 ± 12.20 |
| 20 | ① | 45.38 ± 21.52 |
| | ② | 65.58 ± 21.94 |
| | ③ | 98.93 ± 2.15 |
| | ④ | 29.83 ± 16.05 |
| 24 | ① | 54.63 ± 27.65 |
| | ② | 81.98 ± 13.26 |
| | ③ | 100.00 ± 0.00 |
| | ④ | 34.58 ± 22.34 |
| 28 | ① | 70.60 ± 18.38 |
| | ② | 86.63 ± 16.19 |
| | ③ | 100.00 ± 0.00 |
| | ④ | 50.30 ± 18.27 |
| 32 | ① | 81.08 ± 16.18 |
| | ② | 93.08 ± 10.94 |
| | ③ | 100.00 ± 0.00 |
| | ④ | 56.60 ± 15.32 |
| 36 | ① | 95.73 ± 6.08 |
| | ② | 100.00 ± 0.00 |
| | ③ | 100.00 ± 0.00 |
| | ④ | 66.38 ± 26.64 |
| 46 | ① | 100.00 ± 0.00 |
| | ② | 100.00 ± 0.00 |
| | ③ | 100.00 ± 0.00 |
| | ④ | 90.63 ± 12.15 |
| 56 | ① | 100.00 ± 0.00 |
| | ② | 100.00 ± 0.00 |
| | ③ | 100.00 ± 0.00 |
| | ④ | 93.90 ± 8.72 |

<Data Analysis>

The data were analyzed in the same manner as in Example 4 or 5. Based on the results shown in Table 5 and FIG. 12, the "Healing Rate" was calculated using as "Standard Area" the size in the area of damaged cornea which was measured 6 hours after the model animal was prepared. The formula shown in Example 4 was used for said calculation.

The results described above indicate that the model animal and screening method of the invention were adequate as an assay system or a method to evaluate the therapeutic effects of medicines.

Comparative Example 3

Use of the Comparative Model Animal Example 1 for Evaluation of Medicine

The tests were carried out in the same manner as in Examples 4 to 6 by the use of the comparative model animal example 1 shown in Comparative Example 1.

<Administration of a Medicine>

Hyalein was used as a medicine to be tested. The tests were carried out in the same manner as described in Examples 4 to 6, using 4 groups of animals and four eyeballs (right and left eyeballs of two animals) per group. One drop (about 50 micro liters) of Hyalein was instilled repeatedly to the eyeballs of animals in Groups 1 to 3 and a physiological saline solution to Group 4.

In the same manner as in Examples 4 to 6, administration of the medicine was discontinued when the recovery of the corneal damages was observed, and the animal was considered to have recovered from the disease when no damaged area of cornea was observed.

<Measurement of Damaged Area>

Figure 14:
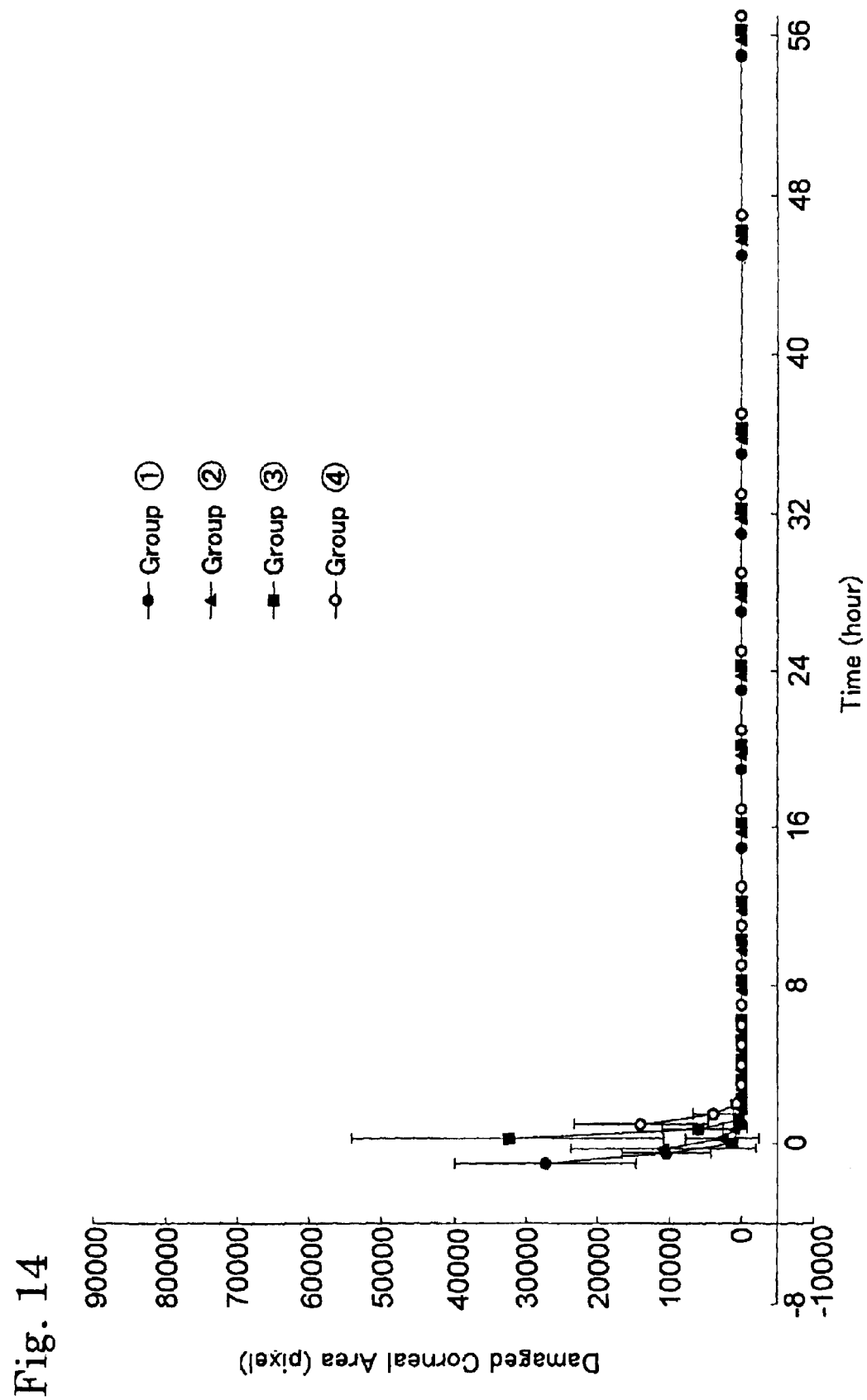
FIG. 14 is a graph showing a sequential change of the damaged corneal area measured according to Comparative Example 2.

The damaged area was measured in the same manner as in Examples 4 to 6, and the sequential changes in the damaged area of the cornea are shown in Table 7 and FIG. 14.

TABLE 7

Sequential Change of The Damaged Corneal Area

| Time (hour) | Group | Damaged Corneal Area (pixel) Average ± Standard deviation |
|---|---|---|
| 0 | ① | 27279.0 ± 12618.2 |
| | ② | 10855.5 ± 12866.8 |
| | ③ | 32416.0 ± 21687.5 |
| | ④ | 14007.8 ± 9316.0 |
| 0.5 | ① | 10442.3 ± 5180.1 |
| | ② | 5959.0 ± 5048.1 |
| | ③ | 3907.5 ± 2742.6 |
| | ④ | 1352.5 ± 775.2 |
| 1 | ① | 867.8 ± 1735.5 |
| | ② | 338.3 ± 676.5 |
| | ③ | 881.0 ± 840.1 |
| | ④ | 0.0 ± 0.0 |
| 2 | ① | 0.0 ± 0.0 |
| | ② | 0.0 ± 0.0 |
| | ③ | 0.0 ± 0.0 |
| | ④ | 0.0 ± 0.0 |
| 3 | ① | 0.0 ± 0.0 |
| | ② | 0.0 ± 0.0 |
| | ③ | 0.0 ± 0.0 |
| | ④ | 0.0 ± 0.0 |
| 4 | ① | 0.0 ± 0.0 |
| | ② | 0.0 ± 0.0 |
| | ③ | 0.0 ± 0.0 |
| | ④ | 0.0 ± 0.0 |
| 5 | ① | 0.0 ± 0.0 |
| | ② | 0.0 ± 0.0 |
| | ③ | 0.0 ± 0.0 |
| | ④ | 0.0 ± 0.0 |
| 6 | ① | 0.0 ± 0.0 |
| | ② | 0.0 ± 0.0 |
| | ③ | 0.0 ± 0.0 |
| | ④ | 0.0 ± 0.0 |
| 8 | ① | 0.0 ± 0.0 |
| | ② | 0.0 ± 0.0 |
| | ③ | 0.0 ± 0.0 |
| | ④ | 0.0 ± 0.0 |
| 10 | ① | 0.0 ± 0.0 |
| | ② | 0.0 ± 0.0 |
| | ③ | 0.0 ± 0.0 |
| | ④ | 20719.8 ± 10124.2 |
| 12 | ① | 0.0 ± 0.0 |
| | ② | 0.0 ± 0.0 |
| | ③ | 0.0 ± 0.0 |
| | ④ | 0.0 ± 0.0 |
| 16 | ① | 0.0 ± 0.0 |
| | ② | 0.0 ± 0.0 |
| | ③ | 0.0 ± 0.0 |
| | ④ | 0.0 ± 0.0 |
| 20 | ① | 0.0 ± 0.0 |
| | ② | 0.0 ± 0.0 |
| | ③ | 0.0 ± 0.0 |
| | ④ | 0.0 ± 0.0 |
| 24 | ① | 0.0 ± 0.0 |
| | ② | 0.0 ± 0.0 |

TABLE 7-continued

Sequential Change of The Damaged Corneal Area

| Time (hour) | Group | Damaged Corneal Area (pixel) Average ± Standard deviation |
|---|---|---|
| 28 | ③ | 0.0 ± 0.0 |
|  | ④ | 0.0 ± 0.0 |
|  | ① | 0.0 ± 0.0 |
|  | ② | 0.0 ± 0.0 |
|  | ③ | 0.0 ± 0.0 |
|  | ④ | 0.0 ± 0.0 |
| 32 | ① | 0.0 ± 0.0 |
|  | ② | 0.0 ± 0.0 |
|  | ③ | 0.0 ± 0.0 |
|  | ④ | 0.0 ± 0.0 |
| 36 | ① | 0.0 ± 0.0 |
|  | ② | 0.0 ± 0.0 |
|  | ③ | 0.0 ± 0.0 |
|  | ④ | 0.0 ± 0.0 |
| 46 | ① | 0.0 ± 0.0 |
|  | ② | 0.0 ± 0.0 |
|  | ③ | 0.0 ± 0.0 |
|  | ④ | 0.0 ± 0.0 |
| 56 | ① | 0.0 ± 0.0 |
|  | ② | 0.0 ± 0.0 |
|  | ③ | 0.0 ± 0.0 |
|  | ④ | 1676.5 ± 2258.6 |

<Data Analysis>

Table 7 and FIG. 14 indicate that, unlike the model animal example 1 of the invention, the comparative model animal example 1 began to recover gradually from the disease immediately after the model animal was prepared. They also indicate that the healing of the damaged cornea in the comparative model animal example 1 was so fast that the therapeutic effects of the medicine could hardly be evaluated by the use of said model.

Figure 15:
FIG. 15 is a photographic image of a typical ocular sample of the comparative model animal example 1 (the photograph was taken immediately after the model animal was made).

The photographic image of a typical ocular sample, which was taken by a digital camera immediately after the comparative model animal example 1 was prepared, is to shown in FIG. 15. This indicates that the epithelial damages, i.e., the area stained with sodium fluorescein, formed on the ocular surface of the comparative animal model example 1 were of varied shapes in contrast to those observed in FIG. 7 of Example 5.

Figure 16:
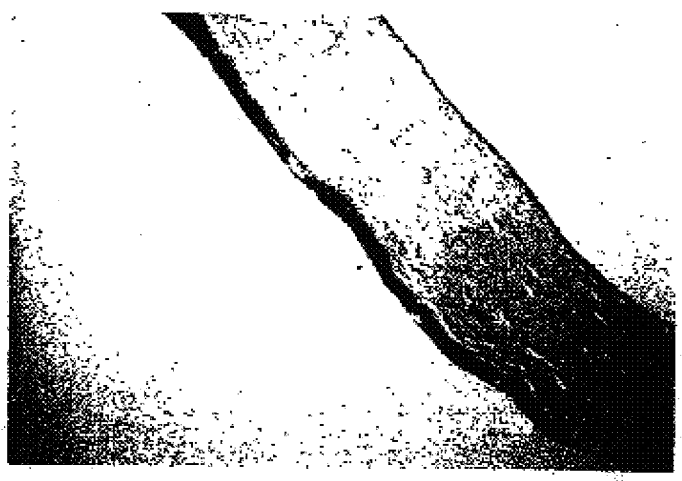
FIG. 16 is a H-E staining image (photographic magnifying powder of 100) of a corneal section of the comparative model animal example 2 (the photograph was taken immediately after the model animal was made).
Figure 17:
FIG. 17 is a H-E staining image (photographic magnifying power of 400) of a corneal section of the comparative model animal example 2 (the photograph was taken immediately after the model animal was made).

The photographic images of corneal sections stained with hematoxylin-eosin (H-E), which were taken immediately after the comparative model animal example 1 was prepared, are shown in FIG. 16 (photographic magnifying power of 100) and FIG. 17 (photographic magnifying power of 400). These images indicate that the corneal epithelium cells in the comparative model animal example 1 were injured, abraded and damaged, but said damages were not so serious and of varied shapes in contrast to those observed in FIG. 8 and FIG. 9 of Example 5.

In the comparative example 1, the model animal was prepared by air-drying the corneal surface of the compulsive eyelid retraction model. In this model animal, the corneal damages were caused by dehydrating the surface of cornea but not from the inside of epithelium cells. Thus, the damages themselves were moderate and healed relatively rapidly.

Comparative Example 4

Use of the Comparative Model Animal Example 2 for Evaluation of Medicine

The tests were carried out in the same manner as in Examples 4 to 6 by the use of the comparative model animal example 2 shown in Comparative Example 2.

<Administration of a Medicine>

Hyalein was used as a medicine to be tested. The tests were carried out in the same manner as described in Examples 4 to 7, using 4 groups of animals and four eyeballs (right and left eyeballs of two animals) per group. One drop (about 50 micro liters) of Hyalein was instilled repeatedly to the eyeballs of animals in Groups 1 to 3 and a physiological saline solution to Group 4.

In the same manner as in Examples 4 to 7, administration of the medicine was discontinued when the recovery of the corneal damages was observed, and the animal was considered to have recovered from the disease when no damaged area of cornea was observed.

<Measurement of Damaged Area>

Figure 18:
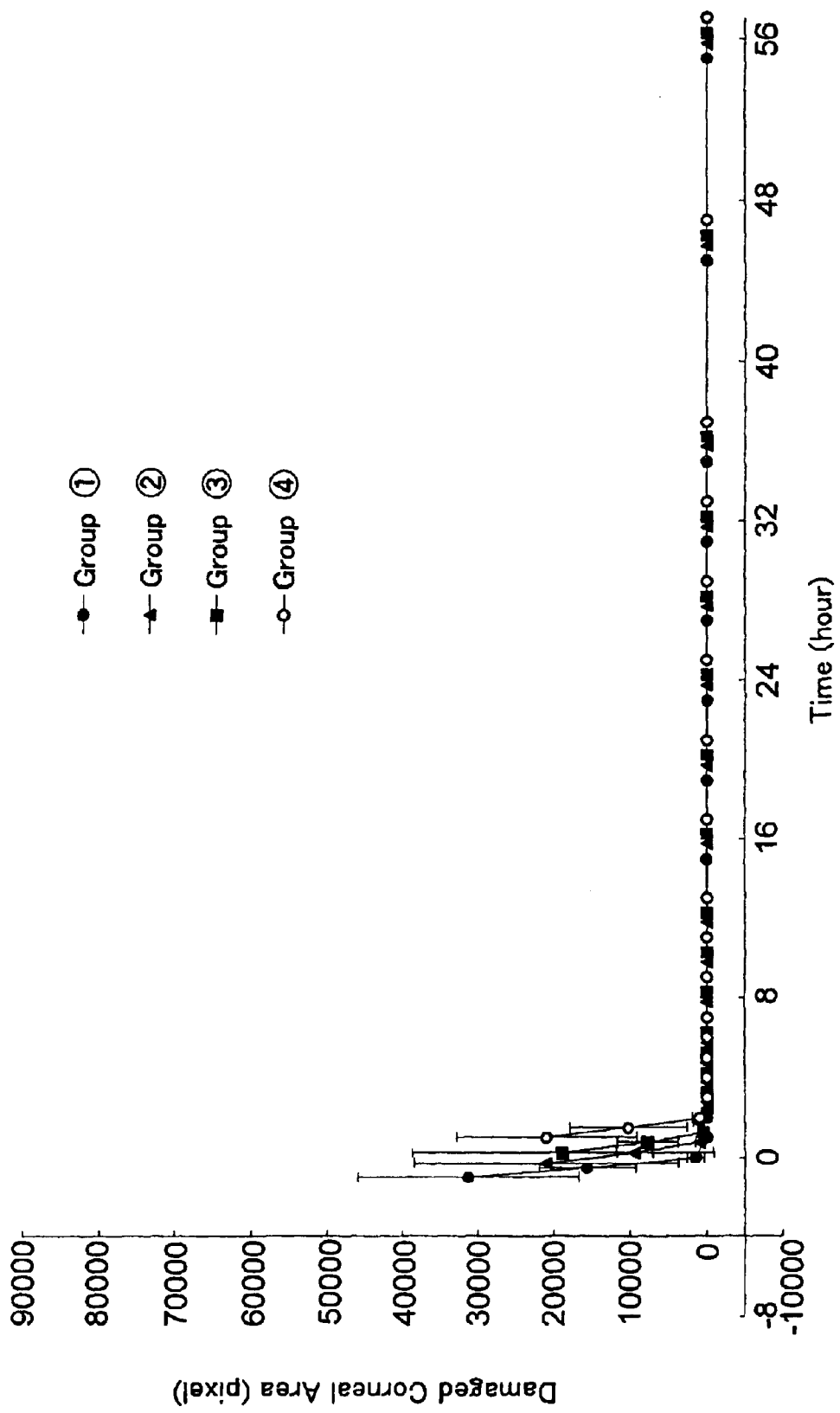
FIG. 18 is a graph showing a sequential change of the damaged corneal area measured according to Comparative Example 4.

The damaged area was measured in the same manner as in Examples 4 to 7, and the sequential changes in the damaged area of the cornea are shown in Table 8 and FIG. 18.

TABLE 8

Sequential Change of The Damaged Corneal Area

| Time (hour) | Group | Damaged Corneal Area (pixel) Average ± Standard deviation |
|---|---|---|
| 0 | ① | 31274.9 ± 14571.2 |
|  | ② | 21060.2 ± 17381.9 |
|  | ③ | 18925.1 ± 19732.0 |
|  | ④ | 20989.0 ± 11823.5 |
| 0.5 | ① | 15620.1 ± 6392.7 |
|  | ② | 9443.0 ± 2354.9 |
|  | ③ | 7691.7 ± 3984.1 |
|  | ④ | 10237.5 ± 7623.0 |
| 1 | ① | 1456.2 ± 1136.8 |
|  | ② | 888.2 ± 599.2 |
|  | ③ | 472.9 ± 451.7 |
|  | ④ | 982.1 ± 883.0 |
| 2 | ① | 0.0 ± 0.0 |
|  | ② | 0.0 ± 0.0 |
|  | ③ | 0.0 ± 0.0 |
|  | ④ | 0.0 ± 0.0 |
| 3 | ① | 0.0 ± 0.0 |
|  | ② | 0.0 ± 0.0 |
|  | ③ | 0.0 ± 0.0 |
|  | ④ | 0.0 ± 0.0 |
| 4 | ① | 0.0 ± 0.0 |
|  | ② | 0.0 ± 0.0 |
|  | ③ | 0.0 ± 0.0 |
|  | ④ | 0.0 ± 0.0 |
| 5 | ① | 0.0 ± 0.0 |
|  | ② | 0.0 ± 0.0 |
|  | ③ | 0.0 ± 0.0 |
|  | ④ | 0.0 ± 0.0 |
| 6 | ① | 0.0 ± 0.0 |
|  | ② | 0.0 ± 0.0 |
|  | ③ | 0.0 ± 0.0 |
|  | ④ | 0.0 ± 0.0 |
| 8 | ① | 0.0 ± 0.0 |
|  | ② | 0.0 ± 0.0 |
|  | ③ | 0.0 ± 0.0 |
|  | ④ | 0.0 ± 0.0 |
| 10 | ① | 0.0 ± 0.0 |
|  | ② | 0.0 ± 0.0 |
|  | ③ | 0.0 ± 0.0 |
|  | ④ | 20719.8 ± 10124.2 |
| 12 | ① | 0.0 ± 0.0 |
|  | ② | 0.0 ± 0.0 |
|  | ③ | 0.0 ± 0.0 |
|  | ④ | 0.0 ± 0.0 |
| 16 | ① | 0.0 ± 0.0 |
|  | ② | 0.0 ± 0.0 |
|  | ③ | 0.0 ± 0.0 |
|  | ④ | 0.0 ± 0.0 |
| 20 | ① | 0.0 ± 0.0 |
|  | ② | 0.0 ± 0.0 |

TABLE 8-continued

Sequential Change of The Damaged Corneal Area

| Time (hour) | Group | Damaged Corneal Area (pixel) Average ± Standard deviation |
|---|---|---|
|  | ③ | 0.0 ± 0.0 |
|  | ④ | 0.0 ± 0.0 |
| 24 | ① | 0.0 ± 0.0 |
|  | ② | 0.0 ± 0.0 |
|  | ③ | 0.0 ± 0.0 |
|  | ④ | 0.0 ± 0.0 |
| 28 | ① | 0.0 ± 0.0 |
|  | ② | 0.0 ± 0.0 |
|  | ③ | 0.0 ± 0.0 |
|  | ④ | 0.0 ± 0.0 |
| 32 | ① | 0.0 ± 0.0 |
|  | ② | 0.0 ± 0.0 |
|  | ③ | 0.0 ± 0.0 |
|  | ④ | 0.0 ± 0.0 |
| 36 | ① | 0.0 ± 0.0 |
|  | ② | 0.0 ± 0.0 |
|  | ③ | 0.0 ± 0.0 |
|  | ④ | 0.0 ± 0.0 |
| 46 | ① | 0.0 ± 0.0 |
|  | ② | 0.0 ± 0.0 |
|  | ③ | 0.0 ± 0.0 |
|  | ④ | 0.0 ± 0.0 |
| 56 | ① | 0.0 ± 0.0 |
|  | ② | 0.0 ± 0.0 |
|  | ③ | 0.0 ± 0.0 |
|  | ④ | 1676.5 ± 2258.6 |

<Data Analysis>

Table 8 and FIG. 18 indicate that, like the comparative model animal example 1, the comparative model animal example 2 began to recover gradually from the disease immediately after the model animal was prepared. They also indicate that the healing of the damaged cornea in the comparative model animal example 1 was so fast that the therapeutic effects of the medicine could hardly be evaluated by the use of said model. In the comparative example 1, the model animal was prepared by air-drying the corneal surface of the compulsive eyelid retraction model.

In this model animal, the corneal damages were caused by dehydrating the surface of cornea, but not the inside of epithelium cells. Thus, like those of the comparative model animal example 1, the damages themselves were moderate and healed relatively rapidly.

It can be seen from the aforementioned Examples 1 to 6 and Comparative Examples 1 to 4 that:

(1) the model animals (e.g., those of Examples 1 to 3) of the invention can maintain the corneal damages for a period of time (e.g., not less than 10 hours) sufficient to evaluate the therapeutic effects of medicines, whereas the comparative model animals are not so suitable for use in such evaluation due to short duration of corneal damages;

(2) the model animals of the invention give rise to uniform epithelial damages with a pre-selected shape on the ocular surface (see, for example, FIG. 7 of Example 5), whereas the known model animal does not generate such uniform damages on the ocular surface and also said damages are of varied shapes (see, for example, FIG. 15 of Comparative Example 3);

(3) the corneal epithelial damages in the model animal of the invention are extensive enough (e.g., corneal abrasion) to evaluate the therapeutic effects of medicines, whereas said damages in the known model animal were rather moderate (see, for example, FIGS. 8 to 11 of Example 5 and FIGS. 16 & 17 of Comparative Example 3);

(4) the model animals (e.g., the model animal examples 1 to 3) of the invention can be prepared within a short period of time, e.g., 20 minutes, whereas the known method requires 3 hours or longer to prepare the comparative model animal example 1; and (5) a model animal having the corneal epithelial damages, suitable for evaluating the therapeutic effects of medicines, can not be prepared by the use of a water-absorbing material which simply absorbs or dehydrate from the ocular surface without generating the difference in osmotic pressure between the inside and outside of epithelium cells (see, for example, Comparative Example 2 or 4).

Further, it can be seen from the foregoing that the model animal of the present invention enables a person engaged in the field of this art to quantitatively evaluate the effects of each medicines on the epithelial damages such as dry eye, e.g., in terms of ED50, and thus is useful as an assay system to screen a variety of new medicines for treatment of said damages. It can also be seen that, according to the present invention, a variety of model animals having different severity of symptoms may be prepared by changing the water-absorbing material, or by changing the time, size, or method (e.g., through semi-permeable membrane) of contact of the water-absorbing material with the corneal surface of the animal.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An experimental animal having corneal epithelial damage in a part of the ocular cornea or in the pupil area of the ocular cornea, wherein said experimental animal is a non-human mammal or a fowl, wherein said corneal epithelial damage is caused by contacting a part or a pupil area of the ocular cornea of said animal with at least one water-absorbing material selected from the group consisting of a polyol, an amino acid, a peptide and a water-soluble polymer, said water-absorbing material being used in the physical state of powder, gel, jelly or tablet, and thereby generating a difference in osmotic pressure between the inside and outside of the ocular corneal epithelium cells.

2. The experimental animal claimed in claim 1, wherein said mammal is rabbit.

3. The experimental animal claimed in claim 1, wherein said water-absorbing material is a saccharide.

4. The experimental animal claimed in claim 1, wherein said water-absorbing material is at least one saccharide selected from the group consisting of glucose, maltose, sucrose, fructose, dextran and starch.

5. An experimental animal having corneal epithelial damage, wherein said experimental animal is a non-human mammal or a fowl, wherein said corneal epithelial damage is caused by covering the ocular cornea of said animal with a water-impermeable membrane or film having a hole or holes in it, said membrane or film being placed on the ocular cornea so that the hole or holes in the membrane or film comes on around the pupil area thereof, contacting the whole area of the ocular cornea or a part thereof, or a pupil area of the ocular cornea of said animal with a water-absorbing material through said hole or holes of the membrane or film and thereby generating a difference in osmotic pressure between the inside and outside of the ocular corneal epithelium cells.

6. The experimental animal claimed in claim 5, wherein said mammal is rabbit.

7. The experimental animal claimed in claim 5, wherein said water-absorbing material is at least one of materials selected from the group consisting of a polyol, a salt, an amino acid, a peptide and a water-soluble polymer.

8. The experimental animal claimed in claim 5, wherein said water-absorbing material is at least one of materials selected from the group consisting of a saccharide, an alkali metal salt and an alkali earth metal salt.

9. The experimental animal claimed in claim 5, wherein said water-absorbing material is at least one saccharide selected from the group consisting of glucose, maltose, sucrose, fructose, dextran and starch.

10. The experimental animal claimed in claim 5, wherein said water-absorbing material is used in the physical state selected from powder, solution, gel, jelly or tablet.

11. An experimental animal having corneal epithelial damage in a part of the ocular cornea or in the pupil area of the ocular cornea, wherein said experimental animal is a non-human mammal or a fowl, wherein said corneal epithelial damage is caused by contacting a part or a pupil area of the ocular cornea of said animal with at least one water-absorbing material selected from the group consisting of a polyol, an amino acid, a peptide and a water-soluble polymer, said water absorbing material being used in the physical state of powder, gel, jelly or tablet, through a water-permeable or semi-permeable membrane or film and thereby generating a difference in osmotic pressure between the inside and outside of the ocular corneal epithelium cells.

12. The experimental animal claimed in claim 11, wherein said mammal is rabbit.

13. The experimental animal claimed in claim 11, wherein said water-absorbing material is a saccharide.

14. The experimental animal claimed in claim 11, wherein said water-absorbing material is at least one saccharide selected from the group consisting of glucose, maltose, sucrose, fructose, dextran and starch.

15. The experimental animal claimed in claim 1, wherein said animal can be used as a dry eye model.

16. The experimental animal claimed in claim 5, wherein said animal can be used as a dry eye model.

17. The experimental animal claimed in claim 11, wherein said animal can be used as a dry eye model.

18. A method of screening or evaluating a medicine treatment or improvement of a corneal epithelial damage, which comprises the steps of:
   (i) administering a medicine to a damaged ocular cornea of the experimental animal claimed in claim 1; and
   (ii) evaluating a therapeutic effect thereof on the corneal epithelial damage.

19. A method of screening or evaluating a medicine for treatment or improvement of a corneal epithelial damage, which comprises the steps of:
   (i) administering a medicine to a damaged ocular cornea of the experimental animal claimed in claim 5; and
   (ii) evaluating a therapeutic effect thereof on the corneal epithelial damage.

20. A method of screening or a medicine for treatment or improvement of a corneal evaluating epithelial damage, which comprises the steps of:
   (i) administering a medicine to a damaged ocular cornea of the experimental animal claimed in claim 11; and
   (ii) evaluating a therapeutic effect thereof on the corneal epithelial damage.

21. The method claimed in claim 18, wherein said step (ii) comprises the steps of: staining a damaged area of the ocular corneal epithelium either
   (a) after administration of the medicine or
   (b) before and after administration of the medicine; and determining change in the stained area of the ocular corneal epithelium.

22. The method claimed in claim 19, wherein said step (ii) comprises the steps of: staining a damaged area of the ocular corneal epithelium either
   (a) after administration of the medicine or
   (b) before and after administration of the medicine; and determining change in the stained area of the ocular corneal epithelium.

23. The method claimed in claim 20, wherein said step (ii) comprises the steps of: staining a damaged area of the ocular corneal epithelium either
   (a) after administration of the medicine or
   (b) before and after administration of the medicine; and determining change in the stained area of the ocular corneal epithelium.

24. A method of producing an experimental animal having corneal epithelial damage, wherein said experimental animal is a non-human mammal or a fowl, comprising the steps of:
   covering the ocular cornea of said animal with a water-impermeable membrane or film having a hole or holes in it, said membrane or film being placed on the ocular cornea so that the hole or holes in the membrane or film comes on around the pupil area thereof, and contacting the whole area of the ocular cornea or a part thereof, or a pupil area of the ocular cornea of said animal with a water-absorbing material through said hole or holes of the membrane or film and thereby generating a difference in osmotic pressure between the inside and outside of the ocular corneal epithelium cells, wherein said difference in osmotic pressure produces corneal epithelial damage.

25. A method of producing an experimental animal having corneal epithelial damage, wherein said experimental animal is a non-human mammal or a fowl, comprising the step of contacting the whole area of the ocular cornea or a part thereof, or a pupil area of the ocular cornea of said animal with a water-absorbing material through a water-permeable or semi-permeable membrane or film and thereby generating a difference in osmotic pressure between the inside and outside of the ocular corneal epithelium cells, wherein said difference in osmotic pressure produces corneal epithelial damage.

26. A method of producing an experimental animal having corneal epithelial damage, wherein said experimental animal is a non-human mammal or a fowl, comprising the step of:
   contacting a part or a pupil area of the ocular cornea of said animal with at least one water-absorbing material selected from the group consisting of a polyol, an amino acid, a peptide and a water-soluble polymer, said water-absorbing material being used in the physical state of powder, gel, jelly or tablet, and thereby generating a difference in osmotic pressure between the inside and outside of the ocular corneal epithelium cells, wherein said difference in osmotic pressure produces corneal epithelial damage.

27. The method claimed in claim 26, wherein said water-absorbing material is at least one saccharide selected from the group consisting of glucose, maltose, sucrose, fructose, dextran and starch.

28. The method claimed in claim 26, wherein said animal is a rabbit.

* * * * *

(12) INTER PARTES REEXAMINATION CERTIFICATE (0055th)
United States Patent
Katsuyama

(10) Number: US 6,924,413 C1
(45) Certificate Issued: Mar. 24, 2009

(54) EXPERIMENTAL ANIMALS FOR EVALUATION OF THERAPEUTIC EFFECTS ON CORNEAL EPITHELIAL DAMAGES

(75) Inventor: Iwao Katsuyama, Osaka (JP)

(73) Assignee: Biochemical and Pharmacological Laboratories, Inc., Tondabayashi, Osaka Pref (JP)

Reexamination Request:
No. 95/000,248, May 9, 2007

Reexamination Certificate for:
Patent No.: 6,924,413
Issued: Aug. 2, 2005
Appl. No.: 10/043,366
Filed: Jan. 10, 2002

(30) Foreign Application Priority Data

| | | |
|---|---|---|
| Mar. 30, 2001 | (JP) | 2001-101250 |
| Jul. 26, 2001 | (JP) | 2001-226460 |
| Nov. 28, 2001 | (JP) | 2001-363147 |

(51) Int. Cl.
*A01K 67/027* (2006.01)
*A01K 67/00* (2006.01)

(52) U.S. Cl. .......................................................... 800/9
(58) Field of Classification Search ........................ None
See application file for complete search history.

(56) References Cited

U.S. PATENT DOCUMENTS

| | | | |
|---|---|---|---|
| 4,014,334 A | 3/1977 | Theeuwses et al. | |
| 4,051,842 A | 10/1977 | Hazel et al. | |
| 4,271,144 A | 6/1981 | Holly | |
| 4,474,751 A | 10/1984 | Haslam et al. | |
| 6,924,413 B2 | 8/2005 | Katsuyama | |

OTHER PUBLICATIONS

Green et al., "Reduction of Corneal Thickness with Hypertonic Solutions," Amer. J. of Ophthalmology 1973, 75, (3), 507–510.
McCulley, "Ocular Hydrofluoric Acid Burns: Animal Model, Mechanism of Injury and Therapy." Trans. Amer. Ophth. Soc. 1990, 88, 649–684.
Luxenberg, et al., "Reduction of Corneal Edema with Topical Hypertonic Agents." American Journal of Ophthalmology 71, (4), 847–853, 1971.
Hayes, In Toxicology of the Eye, Ear, and Other Special Senses; A.W.Hayes, Eds. Raven Press: 1985; pp. 106 and 130–132 and 139.
Swan, "A Dehydrating Jelly to Clear Corneal Bedewing." A.M.A. Archives of Ophthalmology 1953, 50, (1), 75–77.
Harley, "An Experimental Study . . . Evaluation of Hydrosulphosol . . . Treatment of Ocular Injuries . . . Chemical Burns." Trans. Amer. Ophthalmol. Soc. 1951, 49, 557–594.
Gilbard, et al., "Morphologic Effect of Hyperosmolarity on Rabbit Corneal Epithelium." Ophthalmology 1984, 91, (10), 1205–1212.
Moses, et al., "A Standard Large Wound of the Corneal Epithelium in the Rabbit." Investigative Ophthalmology & Visual Science 1979, 18, (1), 103–106.

*Primary Examiner*—Sharon Turner

(57) ABSTRACT

This invention provides experimental animals suffering corneal epithelial damages, such as dry eye, and methods of using the same to assay a variety of compounds for evaluating the therapeutic effect on the disease, and medicine selected using the method, wherein the corneal epithelial damage is induced by the steps of: using a water-absorbing material having a physical state selected from powder, solution, gel, jelly and tablet, and contacting the absorbing materials with the ocular cornea to generate a difference in osmotic pressure between the inside and outside of ocular corneal epithelium cells.

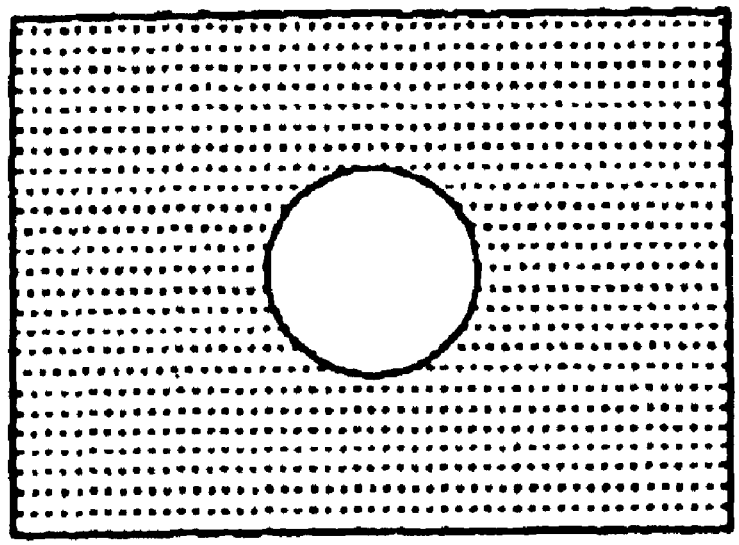

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1–28 are cancelled.

* * * * *